US012806441B2

(12) United States Patent
Dunleavy et al.

(10) Patent No.: US 12,806,441 B2
(45) **Date of Patent: *Nov. 24, 2026**

(54) SYSTEMS AND METHODS FOR TREATING DERMATOLOGICAL IMPERFECTIONS

(71) Applicant: Dermal Photonics Corporation, Middleton, MA (US)

(72) Inventors: Paul Dunleavy, Epping, NH (US); Vladimir Krylov, Brookline, NH (US)

(73) Assignee: NIRA Innovations Incorporated, Danvers, MA (US)

( * ) Notice: Subject to any disclaimer, the term of this patent is extended or adjusted under 35 U.S.C. 154(b) by 845 days.

This patent is subject to a terminal disclaimer.

(21) Appl. No.: 16/883,023

(22) Filed: May 26, 2020

(65) Prior Publication Data

US 2020/0360724 A1 Nov. 19, 2020

Related U.S. Application Data

(60) Continuation of application No. 14/307,938, filed on Jun. 18, 2014, now Pat. No. 10,695,582, which is a (Continued)

(51) Int. Cl.
*A61N 5/06* (2006.01)
*A61N 1/28* (2006.01)
(Continued)

(52) U.S. Cl.
CPC ............. *A61N 5/0625* (2013.01); *A61N 1/28* (2013.01); *A61N 5/0616* (2013.01); (Continued)

(58) Field of Classification Search
CPC ...... A61N 5/0625; A61N 5/0616; A61N 1/28; A61N 2005/0626; A61N 2005/0644; (Continued)

(56) References Cited

U.S. PATENT DOCUMENTS

| | | | |
|---|---|---|---|
| 5,050,597 | A | 9/1991 | Daikuzono |
| 5,735,844 | A | 4/1998 | Anderson et al. |

(Continued)

FOREIGN PATENT DOCUMENTS

| | | |
|---|---|---|
| CN | 101128159 | 2/2008 |
| JP | 2005270125 | 10/2005 |

(Continued)

OTHER PUBLICATIONS

Bean, D., et al., "Treatment of Acne and Wrinkles with Low Power, Double-Pass 1470nm Handheld Laser" Jun. 2011.

(Continued)

*Primary Examiner* — Benjamin J Klein
*Assistant Examiner* — Vynn V Huh
(74) *Attorney, Agent, or Firm* — Onello & Mello P.C.

(57) ABSTRACT

Provided are dermatological medical devices and methods comprising a distal end for positioning at a region proximal a target therapeutic region of tissue, an output port at the distal end, an energy source that generates optical energy, which is output from the output port to the target therapeutic region of tissue, and a control device that controls the optical energy at the target therapeutic region of tissue for increasing a temperature of the target therapeutic region of tissue for a period of time to a temperature that is less than an injurying temperature and induces an expression of heat shock proteins (HSPs) at the target therapeutic region of tissue.

27 Claims, 33 Drawing Sheets

Related U.S. Application Data division of application No. 14/022,372, filed on Sep. 10, 2013, now Pat. No. 8,974,443.

(60) Provisional application No. 61/850,590, filed on Feb. 19, 2013, provisional application No. 61/850,589, filed on Feb. 19, 2013, provisional application No. 61/743,718, filed on Sep. 10, 2012.

(51) Int. Cl.
*G06Q 20/14* (2012.01)
*G06Q 20/22* (2012.01)

(52) U.S. Cl.
CPC ........... *G06Q 20/145* (2013.01); *G06Q 20/22* (2013.01); *A61N 2005/0626* (2013.01); *A61N 2005/0644* (2013.01); *A61N 2005/0654* (2013.01); *A61N 2005/0659* (2013.01)

(58) Field of Classification Search
CPC .... A61N 2005/0654; A61N 2005/0659; A61N 5/06–2005/073; G06Q 20/145; G06Q 20/22; A61B 18/20–18/28; H01S 3/00
USPC ..................................... 607/88–94; 606/2–19
See application file for complete search history.

(56) References Cited

U.S. PATENT DOCUMENTS

| | | | | |
|---|---|---|---|---|
| 6,009,876 | A | 1/2000 | Yavitz | |
| 6,083,217 | A | 7/2000 | Tankovich | |
| 6,161,546 | A | 12/2000 | Yavitz | |
| 6,312,450 | B1 | 11/2001 | Yavitz et al. | |
| 6,514,278 | B1 | 2/2003 | Hibst et al. | |
| 6,663,659 | B2 | 12/2003 | McDaniel | |
| 6,676,655 | B2 | 1/2004 | McDaniel | |
| 7,094,252 | B2 | 8/2006 | Koop | |
| 7,204,832 | B2 | 4/2007 | Altshuler et al. | |
| 7,276,058 | B2 | 10/2007 | Altshuler et al. | |
| 7,303,578 | B2 | 12/2007 | De Taboada et al. | |
| 7,351,252 | B2 | 4/2008 | Altshuler et al. | |
| 7,452,356 | B2 | 11/2008 | Grove et al. | |
| 7,643,883 | B2 | 1/2010 | Kreindel | |
| 7,644,145 | B2 | 1/2010 | Rockwell | |
| 7,749,260 | B2 | 7/2010 | Da Silva et al. | |
| 7,846,191 | B2 | 12/2010 | Vaynberg et al. | |
| 7,887,533 | B2 | 2/2011 | Barolet et al. | |
| 7,914,523 | B2 | 3/2011 | Barolet et al. | |
| D649,636 | S | 11/2011 | Bean et al. | |
| 8,126,784 | B1 | 2/2012 | Agarwal | |
| 8,182,473 | B2 | 5/2012 | Altshuler et al. | |
| 8,202,268 | B1 * | 6/2012 | Wells | A61B 18/22 606/9 |
| 8,523,791 | B2 | 9/2013 | Castel | |
| 8,620,451 | B2 | 12/2013 | Kennedy | |
| 8,888,830 | B2 | 11/2014 | Dunleavy et al. | |
| 8,974,443 | B2 | 3/2015 | Dunleavy et al. | |
| 2004/0077977 | A1 * | 4/2004 | Ella | A61H 23/0245 601/9 |
| 2004/0092919 | A1 | 5/2004 | Ritchie et al. | |
| 2004/0093042 | A1 * | 5/2004 | Altshuler | A61B 18/203 607/88 |
| 2004/0147984 | A1 | 7/2004 | Altshuler et al. | |
| 2004/0162596 | A1 | 8/2004 | Altshuler et al. | |
| 2004/0167499 | A1 | 8/2004 | Grove et al. | |
| 2005/0107850 | A1 | 5/2005 | Vaynberg et al. | |
| 2005/0197681 | A1 | 9/2005 | Barolet et al. | |
| 2005/0222555 | A1 | 10/2005 | Manstein et al. | |
| 2006/0116671 | A1 | 6/2006 | Slayton et al. | |
| 2006/0173518 | A1 | 8/2006 | Kreindel | |
| 2007/0038206 | A1 * | 2/2007 | Altshuler | A46B 15/0036 606/20 |
| 2007/0055327 | A1 | 3/2007 | Esch et al. | |
| 2007/0118098 | A1 | 5/2007 | Tankovich | |
| 2007/0185553 | A1 | 8/2007 | Kennedy | |
| 2008/0031833 | A1 | 2/2008 | Oblong et al. | |
| 2008/0033516 | A1 | 2/2008 | Altshuler et al. | |
| 2008/0051680 | A1 | 2/2008 | Luebcke | |
| 2008/0077200 | A1 | 3/2008 | Bendett et al. | |
| 2008/0091179 | A1 | 4/2008 | Durkin et al. | |
| 2008/0091251 | A1 | 4/2008 | Walneck et al. | |
| 2008/0108982 | A1 | 5/2008 | Barolet et al. | |
| 2008/0140164 | A1 | 6/2008 | Oberreiter et al. | |
| 2008/0147431 | A1 | 6/2008 | Walneck et al. | |
| 2008/0269847 | A1 | 10/2008 | Nemenov | |
| 2009/0040067 | A1 | 2/2009 | McCoy et al. | |
| 2009/0044129 | A1 | 2/2009 | Ebrom et al. | |
| 2009/0044137 | A1 | 2/2009 | Bartley et al. | |
| 2009/0209958 | A1 | 8/2009 | Davison et al. | |
| 2009/0234342 | A1 | 9/2009 | Ely et al. | |
| 2009/0240310 | A1 | 9/2009 | Kennedy | |
| 2009/0254154 | A1 | 10/2009 | De Taboada et al. | |
| 2010/0010480 | A1 | 1/2010 | Mehta et al. | |
| 2010/0049180 | A1 * | 2/2010 | Wells | A61N 5/0616 606/11 |
| 2010/0069898 | A1 | 3/2010 | O'Neil et al. | |
| 2010/0102051 | A1 | 4/2010 | Ebrom et al. | |
| 2010/0106265 | A1 | 4/2010 | Ebrom et al. | |
| 2010/0145321 | A1 | 6/2010 | Altshuler et al. | |
| 2011/0040235 | A1 | 2/2011 | Castel | |
| 2011/0040358 | A1 | 2/2011 | Bean et al. | |
| 2011/0122905 | A1 | 5/2011 | Bean et al. | |
| 2011/0125227 | A1 | 5/2011 | Vaynberg et al. | |
| 2011/0202116 | A1 | 8/2011 | Barolet et al. | |
| 2012/0143288 | A1 | 6/2012 | Owens et al. | |
| 2013/0030423 | A1 | 1/2013 | Reichert et al. | |
| 2014/0074191 | A1 | 3/2014 | Dunleavy et al. | |
| 2014/0074194 | A1 | 3/2014 | Dunleavy et al. | |
| 2014/0114299 | A1 | 4/2014 | Grove et al. | |
| 2014/0364924 | A1 | 12/2014 | Dunleavy et al. | |
| 2015/0058204 | A1 | 2/2015 | Dunleavy et al. | |

FOREIGN PATENT DOCUMENTS

| | | | |
|---|---|---|---|
| JP | 2006518610 | 8/2006 | |
| JP | 2007502141 | 2/2007 | |
| JP | 2007510466 | 4/2007 | |
| JP | 2009028271 | 2/2009 | |
| JP | 2015527177 | 9/2015 | |
| WO | 2004000150 | 12/2003 | |
| WO | 2004033040 | 4/2004 | |
| WO | 2006049570 | 5/2006 | |
| WO | 2010120909 | 10/2010 | |
| WO | WO-2011011644 A2 * | 1/2011 | A61N 5/0616 |
| WO | 2011078905 | 6/2011 | |
| WO | 2012075419 | 6/2012 | |
| WO | 2014040015 | 3/2014 | |

OTHER PUBLICATIONS

Canty, E.G. et al. Procollagen Trafficking, Processing and Fibrillogenesis Journal of Cell Science, Apr. 1, 2005 vol. 118, No. 7 pp. 1341-1353.

Chinese Office Action dated Feb. 26, 2018 issued in corresponding Chinese Office Application No. 201380058774.3, with English language translation.

Chinese Office Action dated Jun. 21, 2017 issued in corresponding Chinese Application No. 201380058774.3.

Chinese Office Action dated Sep. 4, 2018 issued in corresponding Chinese Application No. 201380058774.3, with English translation.

European Office Action dated Mar. 3, 2017; issued in corresponding European Application No. 13 834 522.8.

European Office Action dated Sep. 4, 2017 issued in corresponding European Application No. 13834522.8.

Extended European Search Report dated Apr. 22, 2016 issued in corresponding European Patent Application No. 13834522.8.

Extended European Search Report dated Jun. 17, 2019 issued in corresponding European Application No. 18208500.1.

International Search Report and Written Opinion dated Dec. 6, 2013, issued in International Application No. PCT/US2013/058882.

(56) References Cited

OTHER PUBLICATIONS

International Search Report and Written opinion dated Jun. 22, 2015 issued in International Application No. PCT/US2015/023605.
International Search Report dated Oct. 24, 2013, issued in corresponding International Application No. PCT/US2013/058883.
Japanese Office Action dated Apr. 16, 2019 issued in corresponding Japanese Application No. 2018-109876, with machine translation to English.
Japanese Office Action dated Dec. 3, 2019 issued in corresponding Japanese Application No. 2018-109876, with machine translation to English.
Japanese Office Action dated Dec. 3, 2019 issued in corresponding Japanese Application No. 2018-109876, with machine translation to English (Re-submission with translation and comments provided by assoc).
Japanese Office Action dated Jan. 9, 2018 issued in corresponding Japanese Application No. 2015-531305, with machine translation to English.
Japanese Office Action dated Sep. 5, 2017 issued in corresponding Japanese Application No. 2015-531305, with English language machine translation.
Korean Office Action dated Mar. 21, 2019 issued in corresponding Korean Application No. 10-2015-7008884, with English summary.
Office Action dated Jan. 14, 2014, issued in U.S. Appl. No. 14/022,436.
Office Action issued on Feb. 4, 2014 in corresponding U.S. Appl. No. 14/022,372.
Jun. 12, 2014 Office Action issued on Jun. 12, 2014 in corresponding U.S. Appl. No. 14/022,372.
"Systems and Methods for Treating Dermatological Imperfections" Specification, Drawings and Prosecution History of U.S. Appl. No. 14/307,938, filed Jun. 18, 2014, by Paul Dunleavy, et al., which is stored in the United States Patent and Trademark Office (USPTO).
"Systems and Methods for Treating Dermatological Imperfections" Specification, Drawings and Prosecution History of U.S. Appl. No. 14/022,372, filed Sep. 10, 2013, now U.S. Pat. No. 8,974,443, issued Mar. 10, 2015, by Paul Dunleavy, et al., which is stored in the United States Patent and Trademark Office (USPTO).
Chinese Office Action dated Aug. 25, 2020 issued in corresponding Chinese Application No. 201910299314.9, with English translation.
Japanese Office Action dated Jul. 14, 2020 issued in corresponding Japanese Application No. 2018-109876, with machine translation to English.

* cited by examiner

SYSTEMS AND METHODS FOR TREATING DERMATOLOGICAL IMPERFECTIONS

RELATED APPLICATIONS

This application is a continuation of U.S. patent application Ser. No. 14/307,938, filed Jun. 18, 2014, which is a divisional of U.S. patent application Ser. No. 14/022,372, filed Sep. 10, 2013, U.S. Pat. No. 8,974,443, which claims the benefit of U.S. Provisional Patent Application No. 61/743,718 filed on Sep. 10, 2012, U.S. Provisional Patent Application No. 61/850,590 filed on Feb. 19, 2013, and U.S. Provisional Patent Application No. 61/850,589 filed on Feb. 19, 2013, the content of each of which is incorporated herein by reference in its entirety. This application is related to U.S. patent application Ser. No. 14/022,436, filed Sep. 10, 2013, U.S. Pat. No. 8,888,830, the content of which is incorporated herein by reference in its entirety.

FIELD

Embodiments of the present inventive concepts relates generally to devices, systems, and methods for treating dermatological imperfections, and more specifically, to dermatological medical devices, systems, and methods for performing non-injuring heat shock stimulation of human or animal tissue.

BACKGROUND

As a person ages, the body goes through a slow process of degeneration. The evidence of the aging process becomes physically apparent in the formation of wrinkles and uneven pigmentation on the skin. Wrinkles, in particular, are caused by degeneration of the dermis, muscle contractions and gravity. Uneven pigmentation can occur as a result of aging, sun exposure, or other environmental factors.

The aging process typically includes the loss of collagen in the dermal layer of the skin, which causes the skin to become thinner, and for wrinkles, sagging, or other imperfections to occur.

SUMMARY

According to an aspect of the present inventive concepts, provided are systems, devices, and methods for performing a non-injuring heat shock therapy to soft tissue by integrating an optical energy source that emits optimum wavelengths, an energy dosage, and/or a thermal boost under controlled conditions.

According to another aspect, provided are systems, devices, and methods for integrating a treatment time and usage replenishment business model.

According to an aspect, provided is a dermatological medical device comprising: a distal end for positioning at a region proximal a target therapeutic region of tissue; an output port at the distal end; an energy source that generates optical energy, which is output from the output port to the target therapeutic region of tissue; and a control device that controls the optical energy at the target therapeutic region of tissue for increasing a temperature of the target therapeutic region of tissue for a period of time to a temperature that is less than an injuring temperature and induces an expression of heat shock proteins (HSPs) at the target therapeutic region of tissue.

In some embodiments, the HSPs stimulate collagen synthesis at the target therapeutic region of tissue.

In some embodiments, the dermatological medical device further comprises a housing that encapsulates the energy source and the control device and a power source positioned in the housing that provides a source of electrical energy to the optical energy source.

In some embodiments, the dermatological medical device further comprises a

In some embodiments, the optical energy source outputs the optical energy have at least one of a wavelength, energy dosage, or thermal boost that provides a non-injuring heat shock stimulation at the therapeutic region of tissue depending on the optical properties of the skin and its wavelength.

In some embodiments, the tissue includes human or animal skin.

In some embodiments, the dermatological medical device further comprises at least one safety sensor that determines whether a temperature of at the therapeutic region of tissue is within a predetermined acceptable range, and permits the control device to provide a laser emission and delivery of electrical current to the energy source.

In some embodiments, the dermatological medical device further comprises a contact sensor that includes a safety interlock for registering contact with the tissue.

In some embodiments, dermatological medical device further comprises an optical spatial distribution system (OSDS) that modifies a spatial distribution of the optical energy to a desired distribution at the distal end.

In some embodiments, an amount of therapeutic energy delivered at the target therapeutic region of tissue is controlled by controlling the temporal profile of the delivered energy.

In some embodiments, the dermatological medical device further includes a skin stretching mechanism to reduce optical losses due to wrinkles or tissue folds.

In some embodiments, the device delivers an extended thermal exposure time by providing a thermal boost at the end of the treatment pulse.

In some embodiments, a temperature of the target therapeutic region of tissue is increased by at least 2 °C. and no more than 8 °C.

In some embodiments, an exposure of energy output from the dermatological medical device at the target therapeutic region of tissue is between 2-10 seconds at one or more temperatures less than the injuring temperature.

In some embodiments, a temperature temporal profile of the target therapeutic tissue is controlled by modulating a temporal profile of the energy source.

In some embodiments, a therapeutic energy dosage is controlled by controlling the temporal profile of the delivered energy, and wherein peak powers and exposure time are modulated to provide a desired clinical effect.

According to an aspect, provided is a method for non-injuring heat shock stimulation of human or animal tissue, comprising: positioning a distal end of a handheld dermatological medical device at a region proximal a target therapeutic region of tissue; outputting optical energy from the handheld dermatological medical device at the target therapeutic region of tissue; and controlling the output of optical energy at the target therapeutic region of tissue to increases a temperature of the target therapeutic region of tissue for a period of time to a temperature that is less than an injuring temperature and induces an expression of heat shock proteins (HSPs) at the target therapeutic region of tissue.

In some embodiments, controlling the output of optical energy includes outputting the optical energy to have at least one of a wavelength, energy dosage, or thermal boost that provides a non-injurying heat shock stimulation at the therapeutic region of tissue depending on the optical properties of the skin and its wavelength.

In some embodiments, the method further comprises modifying a spatial distribution of the optical energy to a desired distribution at a distal end of the handheld dermatological medical device.

In some embodiments, the method further comprises controlling a temporal profile of energy delivered to the target therapeutic region of tissue.

In some embodiments, a temperature of the target therapeutic region of tissue is increased by at least 2 °C and no more than 8 °C.

In some embodiments, an exposure of energy output from the dermatological medical device at the target therapeutic region of tissue is between 2-10 seconds at one or more temperatures less than the injurying temperature.

In some embodiments, controlling a temperature temporal profile of the target therapeutic tissue by modulating a temporal profile of an energy source of the optical energy.

In some embodiments, controlling a therapeutic energy dosage by controlling a temporal profile of the delivered energy, and wherein peak powers and exposure time are modulated to provide a desired clinical effect.

According to an aspect, provided is a method for non-injurying heat shock stimulation of human or animal tissue comprising: providing a handheld treatment device with a distal treatment end; and outputting optical energy from the handheld treatment device at the target therapeutic region of tissue, wherein treatment intervals provide a maximum average heat shock protein expression.

In some embodiments, the treatment intervals are 1.5 hours to 48 hours.

According to an aspect, provided is a method for non-injurying heat shock stimulation of human or animal tissue comprising: providing a handheld treatment member with a distal treatment end; and outputting optical energy from the distal treatment end of the handheld treatment device at the target therapeutic region of tissue, wherein the outer surface of the tissue is removed of energy absorbing chromophore prior to an optical energy treatment.

In some embodiments, a water chromophore is reduced from the stratum corneum through aqueous dessecating solution.

In some embodiments, an application of the handheld treatment member is selected from the group consisting of: wrinkle reduction; acne reduction; skin tightening; tissue heating; treatment of fibrous tissue; treatment of vascular tissue; and combinations thereof.

BRIEF DESCRIPTION OF THE DRAWINGS

The accompanying drawings, which are incorporated in and constitute a part of this specification, illustrate various embodiments, and, together with the description, serve to explain the principles of the inventive concepts. In the drawings.

DESCRIPTION OF THE EMBODIMENTS

Figure 1:
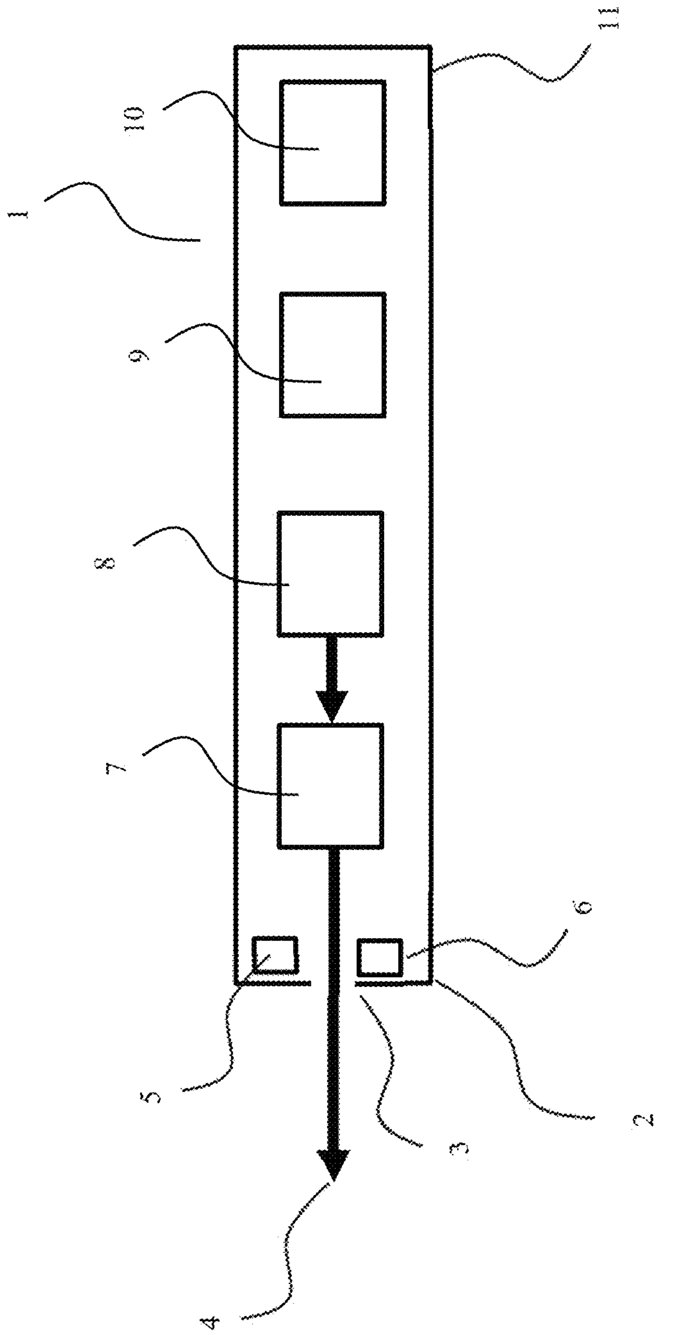
FIG. 1 is a block diagram of a handheld dermatological medical device, in accordance with an embodiment of the present inventive concepts.

Reference will now be made in detail to embodiments of the inventive concepts, examples of which are illustrated in the accompanying drawings. Wherever possible, the same reference numbers will be used throughout the drawings to refer to the same or like parts.

The terminology used herein is for the purpose of describing particular embodiments and is not intended to be limiting of the inventive concepts. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on" or "connected" or "coupled" to another element, it can be directly on or above, or connected or coupled to, the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

Definitions

To facilitate understanding, a number of terms are defined below.

As used herein, the terms "subject" and "patient" refer to any animal, such as a mammal like livestock, pets, and humans. Specific examples of "subjects" and "patients" include, but are not limited, to individuals requiring medical assistance.

As used herein, the terms "skin" and "tissue" refer to any biological tissue that may be intended for treatment or near targeted treatment region of the subject.

Conventional technologies are readily available to enhance collagen production or otherwise address wrinkles or other degenerating skin conditions, and typically include either ablative or non-ablative therapies. Laser ablative therapies use high water absorption and high optical peak power delivered in short pulse durations, causing vaporization of water molecules within the skin. This results in the ablation of one or more layers of the skin, in particular, the epidermis and partially the dermis. The resulting injury requires an extended healing process. Potential side effects such as infections and scars are present. Typical non-ablative therapies include thermal denaturation and thermal coagulation. For example, tissue denaturation occurs when the target tissue is raised to temperatures exceeding 60 °C. Thermal coagulation can occur when the target tissue is raised to temperatures exceeding 50-55 °C. It is well-known to those of ordinary skill in the art that denatured dermal collagen can stimulate collagen synthesis during a period of healing of the tissue exposed to these high temperatures. The safety and effectiveness of laser based thermal therapies relies on selective absorption of the laser energy by chromophores with the target tissue. Chromophores of particular interest include water, lipids, haemoglobin, and melanin. Both ablative and non-ablative laser therapies rely on energy absorption of such chromophores.

Embodiments disclosed herein provide devices, systems, and methods that provide a reliable non-injurying heat shock stimulation of human or animal tissue. In particular, a dermatological medical device can be provided for soft tissue treatments of wrinkle reduction, acne reduction, and/or other degenerating skin conditions addressed by tissue heating, and/or assist in wound healing, skin tightening, and/or the treatment of fibrous tissue, vascular tissue, or related ailments where skin tissue experiences a loss of collagen, or a combination thereof. Additional embodiments disclosed herein provide devices, system and methods for integrating a treatment time and usage replenishment business model.

During an operation, the intended tissue is heated in accordance with an embodiment described herein. In response to heat shock, exposed cells produce heat shock proteins (HSP). HSPs function as molecular chaperones in processes such as protein maturation and degradation and have a protective role in a cell's biological function. HSPs can stimulate collagen synthesis through thermal stimulation and potentially photochemical effects. As laser technology advances, devices and methods to generate HSP response in a cost effective manner become more readily available.

HSPs are named according to their molecular weight in kilo-Daltons, ranging from 10 to 110. HSPs of interest in dermatology can include but not be limited to HSP27, HSP47 and HSP70. HSP27 is an anti-apoptotic protein and protects the cells from death. HSP47 plays an essential role in collagen biosynthesis in skin fibroblasts. HSP70 refers to a highly inducible protein and binds to denatured proteins. For example, tissue exposed to an 815 nm diode laser can result in an HSP70 expression and improved wound healing. One or more HSPs of interest can therefore contribute to a significant slowing down of cellular aging.

Repeated heat shocks of 39 °C to 42 °C with treatment durations of 30 minutes up to 1 hour can result in procollagen type 1 and HSP47 expression. However, long exposure times per treatment site are not practical, and are prevented due to side effects such as damaged tissue and pain. It has also been reported that tissues exposed to less than 45 °C showed no significant change in cell proliferation; hence, no decrease in healing time. Another consideration is that typical conventional devices, both ablative and non-ablative therapies, often produce pain during treatment.

Typically, products and treatment protocols available in the industry require end treatment targets of cellular damage at treatment temperatures well above 45 °C, or above the pain threshold. Typical end treatment target temperatures are above 50 °C for collagen coagulation and beyond 60 °C for tissue denaturation. There is a need for a solution that provides non-injurying treatments with reduced side effects of pain.

In accordance with embodiments of the present inventive concepts, non-injurying treatments are provided by targeting therapeutic temperatures of generating HSPs of 39 °C or higher and below the typical thermal pain threshold of about 45 °C. For purposes of the present disclosure, temperatures greater than the pain threshold of about 45 °C are referred to generally herein as injurying temperatures. Also, the pain threshold for some people may be greater than 45 °C, while the pain threshold for other people may be less than 45 °C. Thus, desirable HSPs can be stimulated without incurring pain. Theoptical energy delivery modalities provided in accordance with embodiments of the present inventive concepts permit a complete solution to be provided that offers greater safety and efficacy within a single device for the treatment of soft tissue. Also, the present inventive concepts permit a device to be used for extended periods of time, for example, over the course of a day, so long as there is sufficient time between treatments to let the tissue cool down after a particular tissue heating operation.

FIG. 1 is a block diagram of a handheld dermatological medical device 1, in accordance with an embodiment of the present inventive concepts.

The device 1 has a distal treatment end 2 that is positioned at a target tissue, for example, a region of skin, to undergo non-injurying heat shock treatment, in accordance with an embodiment. The distal treatment end 2 includes an output port 3 from where optical energy 4 can be output having a wavelength, energy dosage, and/or thermal boost sufficient to provide a non-injurying heat shock stimulation at the target tissue.

The distal treatment end 2 can further be configured to include one or more safety sensors such as one or more contact sensor 5 and/or a thermal sensor 6.

The contact sensor 5 can function as a safety interlock for the purpose of registering contact with the treatment tissue. Laser energy is only emitted when the device is in full contact with the tissue. Contact sensors may utilize measurement of tissue impedance such as capacitance, resistance, inductance or combinations thereof. The contact sensors may be configured exposed electrically conductive contacts to measure resistance or inductance. The sensors may also be configured as capacitors, such that the electrically conductive contacts may have a dielectric insulator between the conductive contact and the tissue. The preferred embodiment utilizes a minimum of three or more contact sensors equally spaced to form a plane around the output port 3. In some embodiments, in order for the device to register full contact with the tissue, all the contact sensors must sense contact. This ensures that output port 3 is fully seated against, and abuts, the treatment tissue during laser emission for laser safety considerations.

Delivering the proper amount of energy to the tissue to achieve the desired temperature change is important to the safety and effectiveness of the treatment. If the energy dosage is not enough, the tissue will not reach the target therapeutic temperatures. If the energy dosage is too high, the tissue temperature increases beyond the pain threshold to potentially denaturation temperatures. Thermal sensors 6 are intended to provide thermal feedback to the device of the tissue temperature. One or more thermal sensors 6 may utilize thermal contact technologies, such as thermocouples or thermistors placed near or at the treatment area. Thermal sensors 6 may also utilize non-contact technologies, such as infrared detectors that are able to detect thermal radiation from the tissue.

In an embodiment, the device 1 can include an optical spatial distribution system (OSDS) 7, an optical energy source 8, control electronics 9, and a power source 10, some or all of which can be positioned in a housing or enclosure 11 that is constructed and arranged to be held by a person performing a medical treatment using the device 1, and which can include an ergonomic and aesthetically pleasing packaging. One or more of the OSDS 7, optical energy source 8, control electronics 9, and power source 10 can include subsystems that are integrated at the enclosure 11.

In some embodiments, the OSDS 7 modifies a spatial distribution of optical energy to a desired distribution at the distal treatment end 2, resulting in the desired treatment effect of the emitted optical energy 4 on the target tissue, for example, the thermal effect on the various skin layers described herein. The OSDS 7 may include but not be limited to a lens system for light focusing, defocusing, peak irradiance homogeneous distribution, and/or a waveguide optic and/or optical filtering.

Figure 28A:
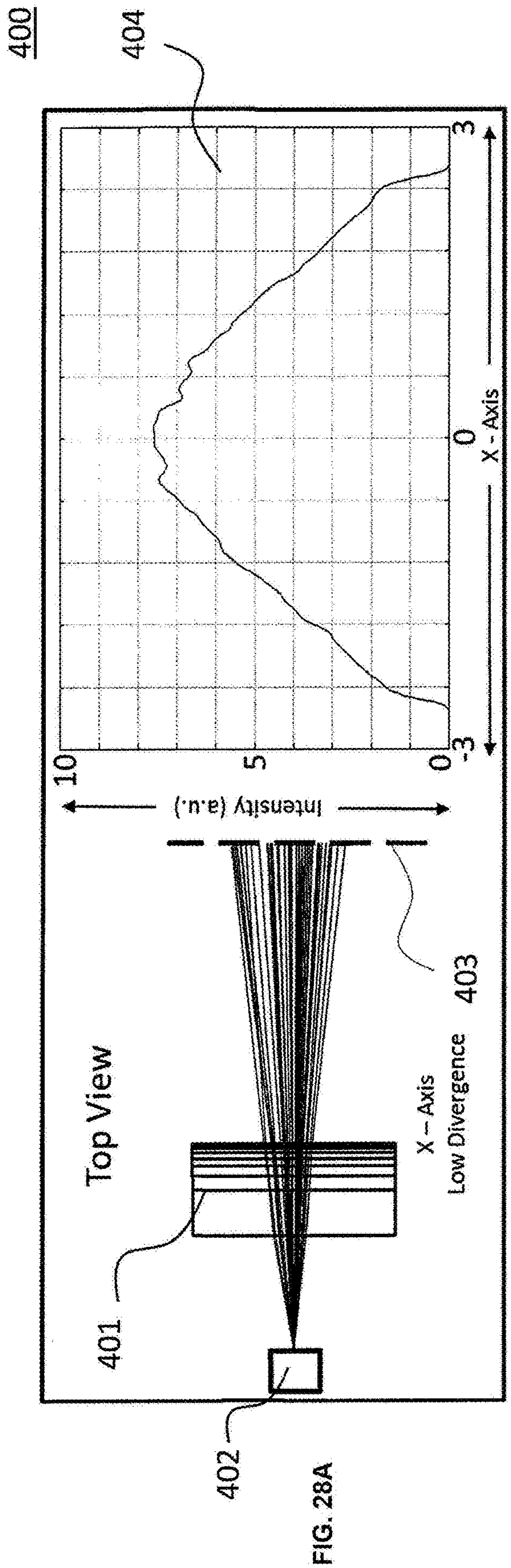
FIG. 28A is a top view of an optical system, in accordance with an embodiment.
Figure 28B:
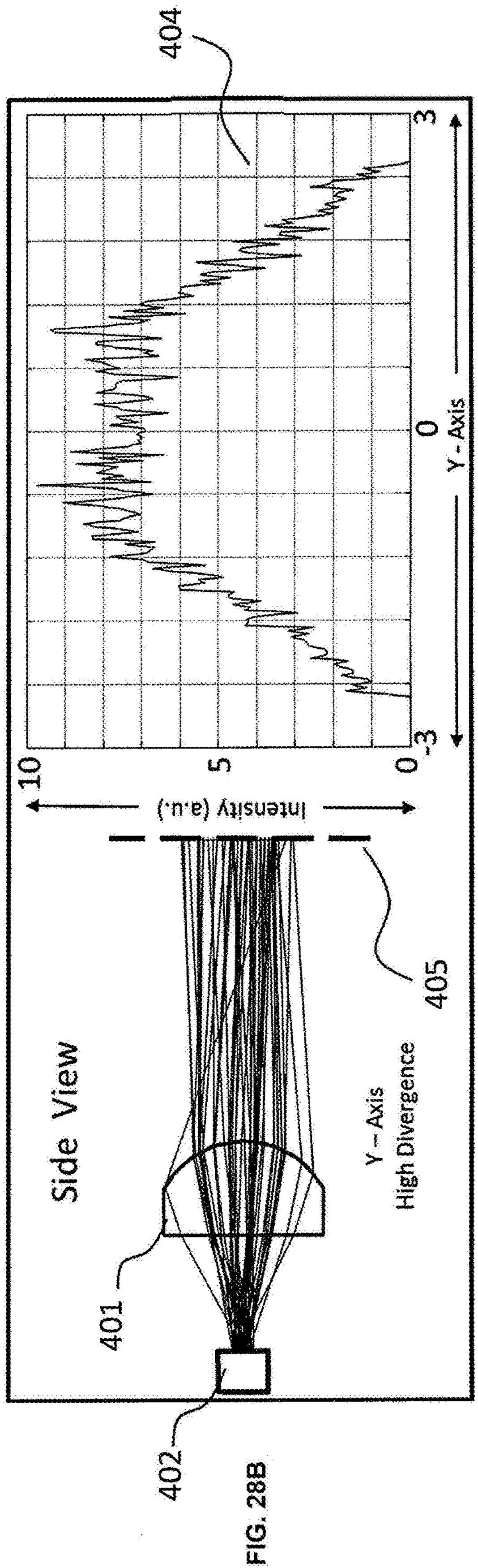
FIG. 28B is a side view of the optical system of FIG. 28A.
Figure 29:
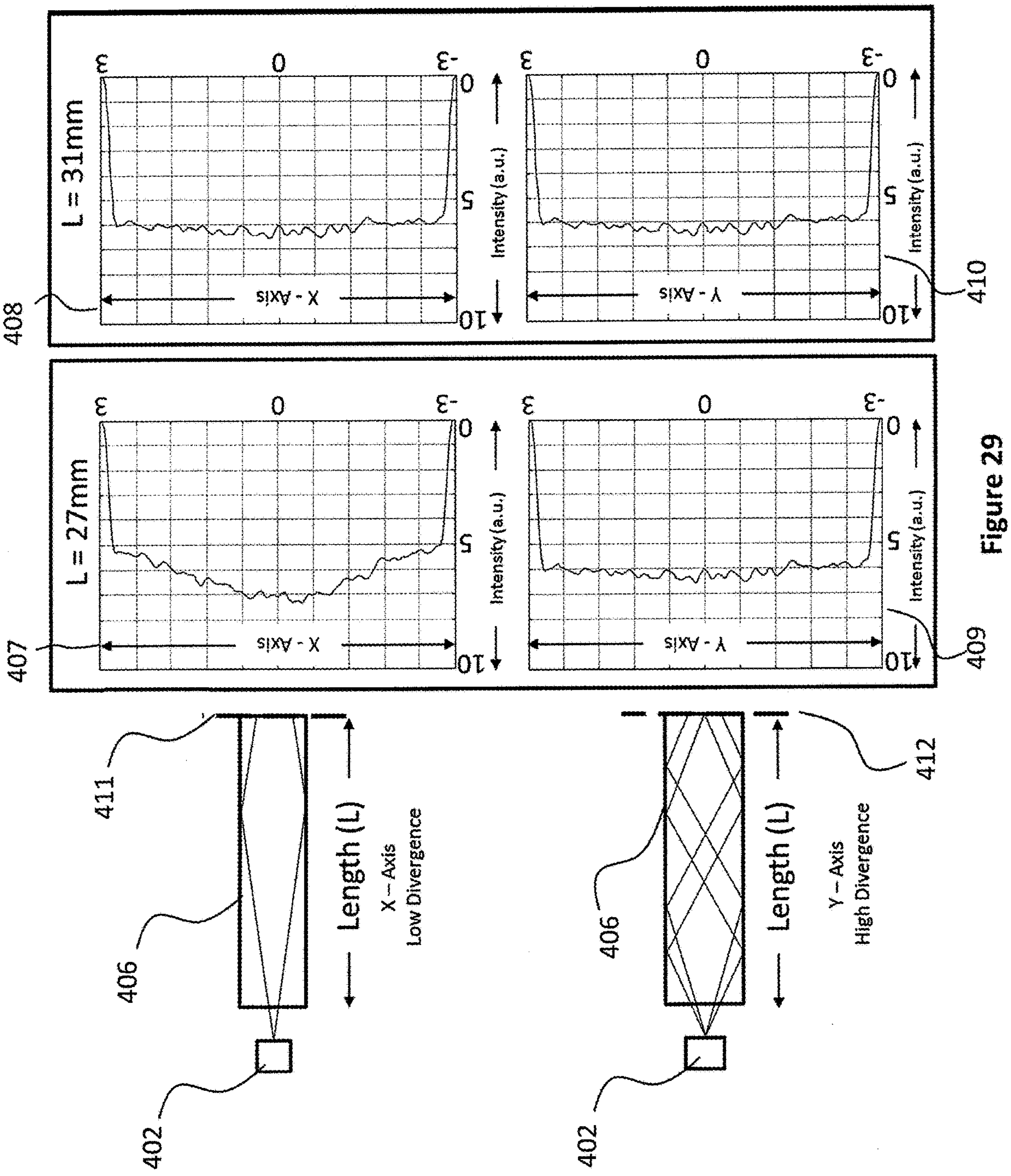
FIG. 29 is a view of an energy source 402 and an optical spatial distribution system (OSDS) having a waveguide, in accordance with an embodiment.

Referring to FIGS. 28A and 28B, a ray trace model in accordance with an embodiment can be provided to include a cylindrical lens as the OSDS 401 and a diode laser as the energy source 402. In particular, FIG. 28A is a top view of an optical system corresponding to the ray trace model. FIG. 28B is a side view of the optical system. In an embodiment, electromagnetic energy, for example, laser energy, propagates from the energy source 402 to the OSDS 401. As shown in the graph, a spatial distribution 404 in the X-axis at a treatment plane 403 is the result of the divergence and angular power distribution of the energy source 402 in the low divergence (X-axis) modified by the OSDS 401. Spatial distribution 404 at treatment plane 405 is the result of the divergence and angular power distribution of the energy source 402 in the high divergence (Y-axis) modified by the OSDS 401. In another embodiment, as shown in FIG. 29, the energy source 402 is shown with a waveguide as the OSDS 406. Spatial distributions shown in graphs 407, 408, 409 and 410 at treatment planes 411 and 412, respectively, are significantly more uniform than the distributions of 402 and 404. The OSDS 406 in FIG. 29 can use total internal reflection to modify the Gaussian angular power distribution of the energy source 402 to a more uniform flat top distribution shown in 407, 408, 409 and 410. In this embodiment, length (L) of the OSDS 406 can be 31 mm or longer to reach uniform flat top distribution 408. At 27 mm, spatial distribution 407 still has a large non-uniform distribution of approximately 30%. The length (L) is driven by the low divergence axis (X-axis) of the energy source 402.

Figure 30:
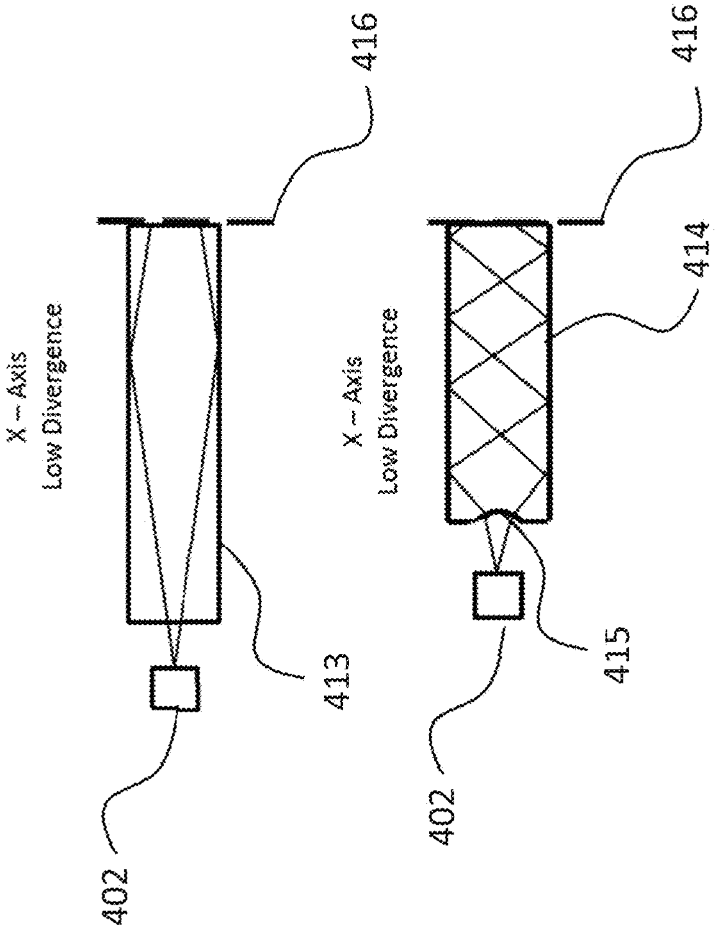
FIG. 30 is a view of a comparison of a standard waveguide and a modified waveguide, in accordance with an embodiment.

FIG. 30 illustrates a comparison of a standard waveguide in an OSDS 413 and a modified waveguide in an OSDS 414. A negative lens curvature 415 can be integrated into the OSDS 414 to increase divergence of the energy source 402, possibly to match the high divergence (Y-axis), to reduce the required length of the OSDS 414 to achieve uniform spatial distribution at treatment plane 416.

Figure 31A:
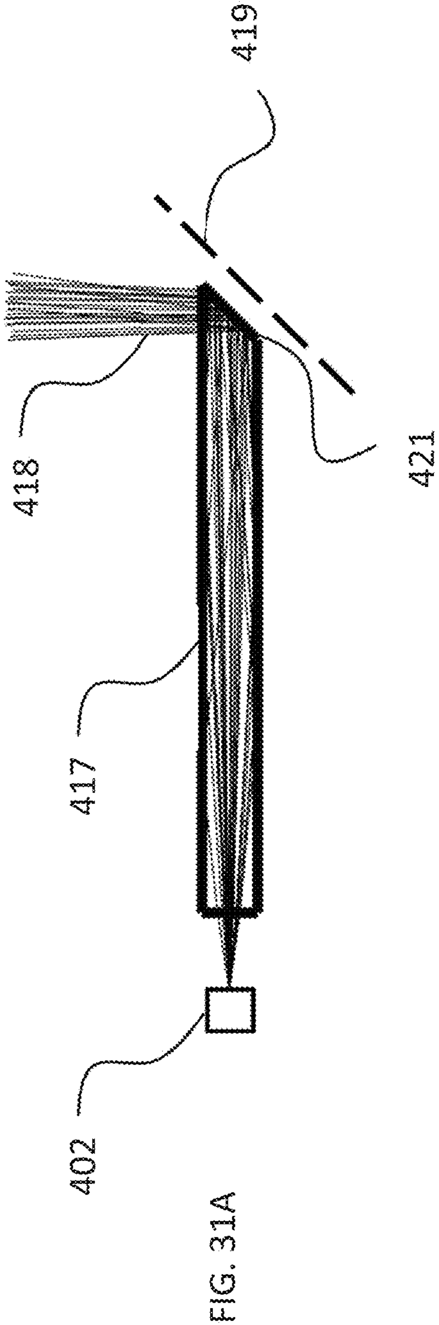
FIG. 31A is a view of an optical spatial distribution system (OSDS) having an angled output surface.
Figure 31B:
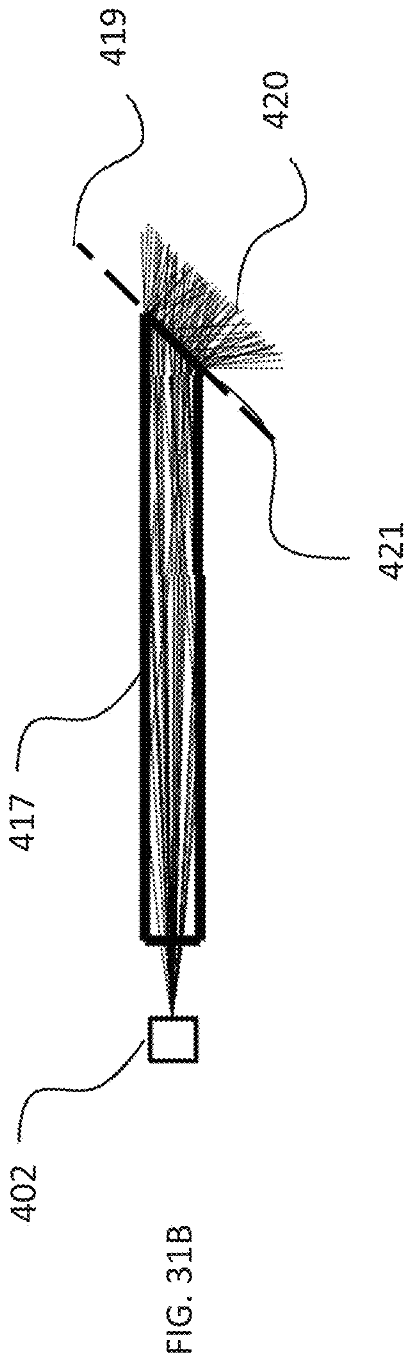
FIG. 31B is a view of the output surface of the OSDS of FIG. 31A in contact with human skin.

In another embodiment, as shown in FIG. 31A, an OSDS 417 has an angled output surface 421. The output surface 421 can reflect >80% of internal light as shown as light leakage 418 when the output surface 421 is in an environment including air, and not in contact with a skin surface 419. Light leakage 418 can be further reduced by applying reflective coating on the surface of the OSDS 417 at the leakage area 418. The light leakage 418 can also be dissipated through the conversion of optical energy to thermal energy by use of an optical absorbing area. In FIG. 31B, the output surface 421 is in contact with the skin 419. The index of refraction at 1440 nm of the human epidermis is approximately 1.41 and the index of refraction of fused silica used in the OSDS 417 is 1.445. When the output surface 421 is in contact with skin 419, the index of refraction is closely matched allowing optical coupling from the OSDS 417 to the skin 419.

Figure 32A:
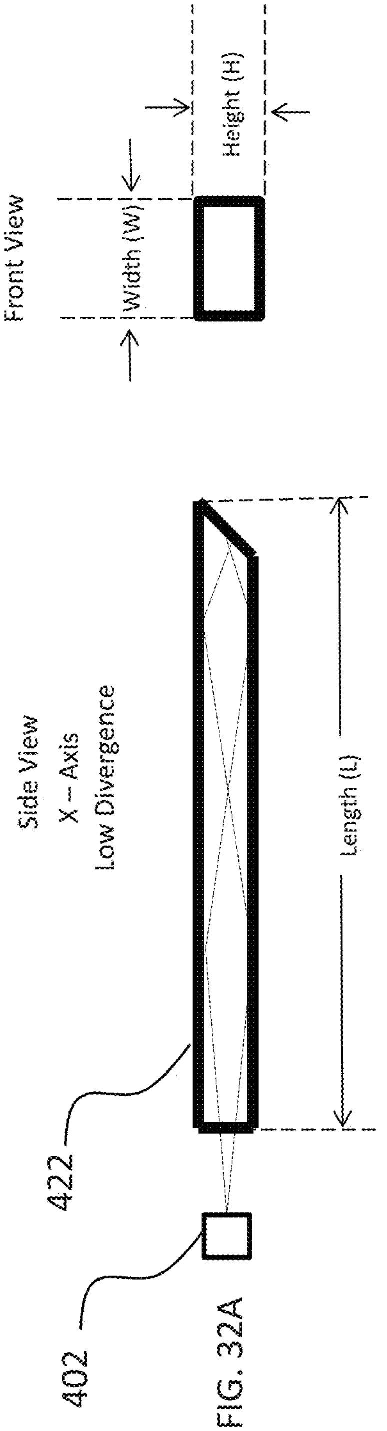
FIGS. 32A and 32B are various views of an OSDS constructed and arranged to achieve total internal reflection, in accordance with an embodiment.
Figure 32B:
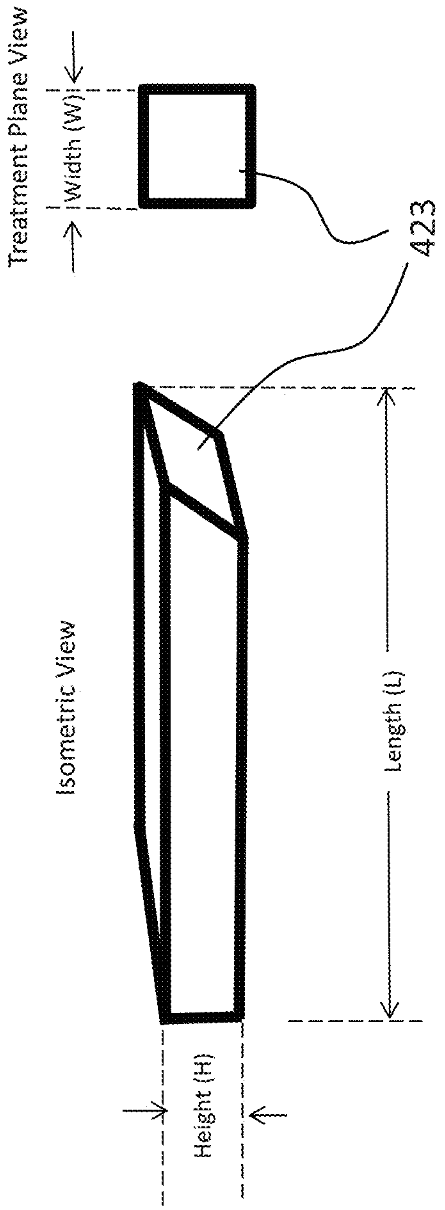

FIGS. 32A, B illustrate another embodiment, in which the height (H) of the OSDS 422 is reduced to achieve total internal reflection with a shortened length (L). In some embodiments, the output surface 423 is angled to provide a substantially square treatment area.

Referring again to FIG. 1, the optical energy source 8 can generate a source of electromagnetic radiation such as light that is output at a target tissue that induce the expression of HSPs in cells of the target tissue, in accordance with an embodiment. The optical energy source 8 can include but not be limited to laser diodes and light emitting diodes. The optical energy source 8 can include but not be limited to other light sources such as near infrared emitting intense pulse light lamps or filament bulbs.

Figure 7:
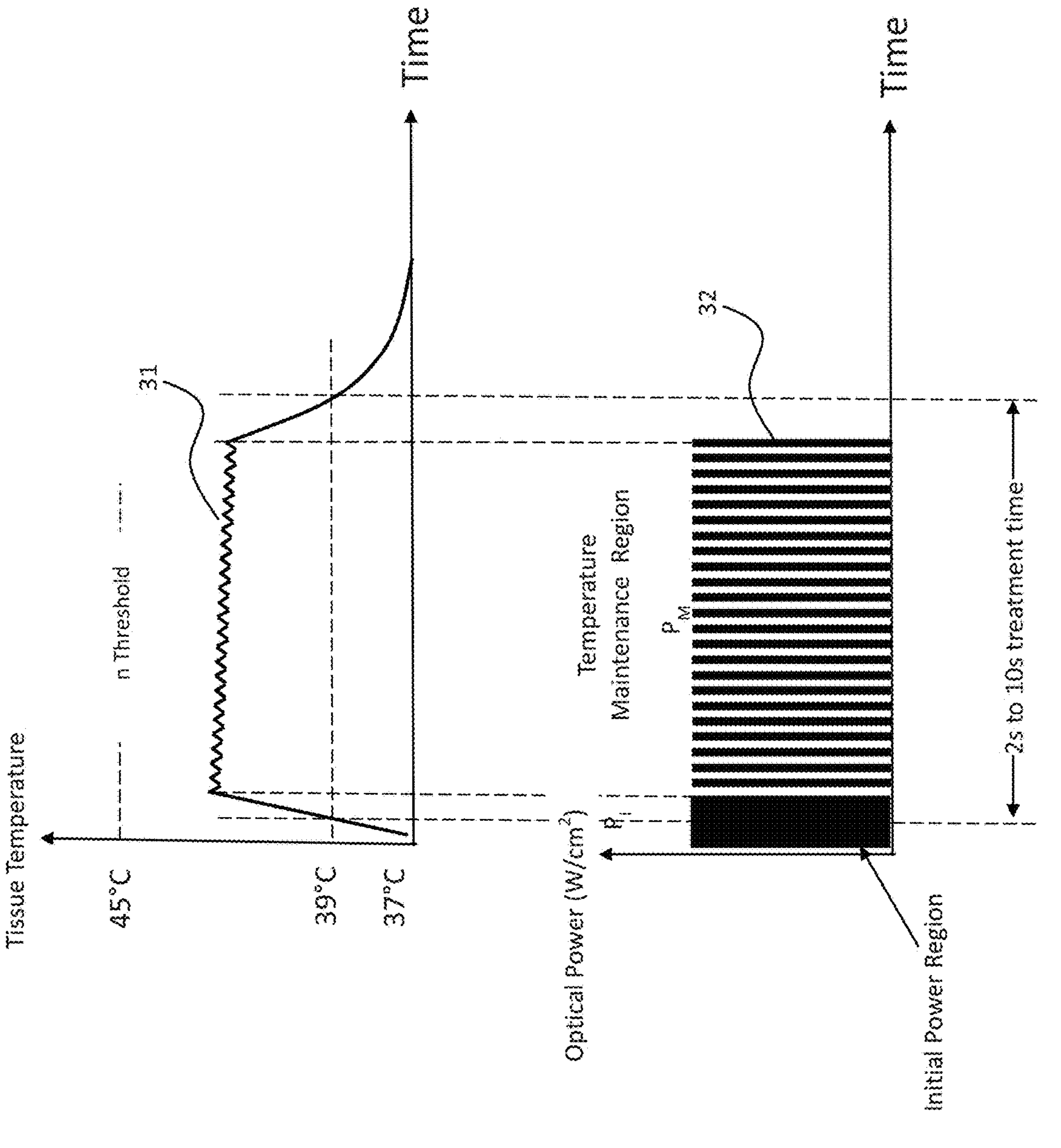
FIG. 7 is a graph illustrating a skin temperature temporal profile relative to an optical power pulsed temporal profile, in accordance with embodiments of the present inventive concepts.
Figure 8:
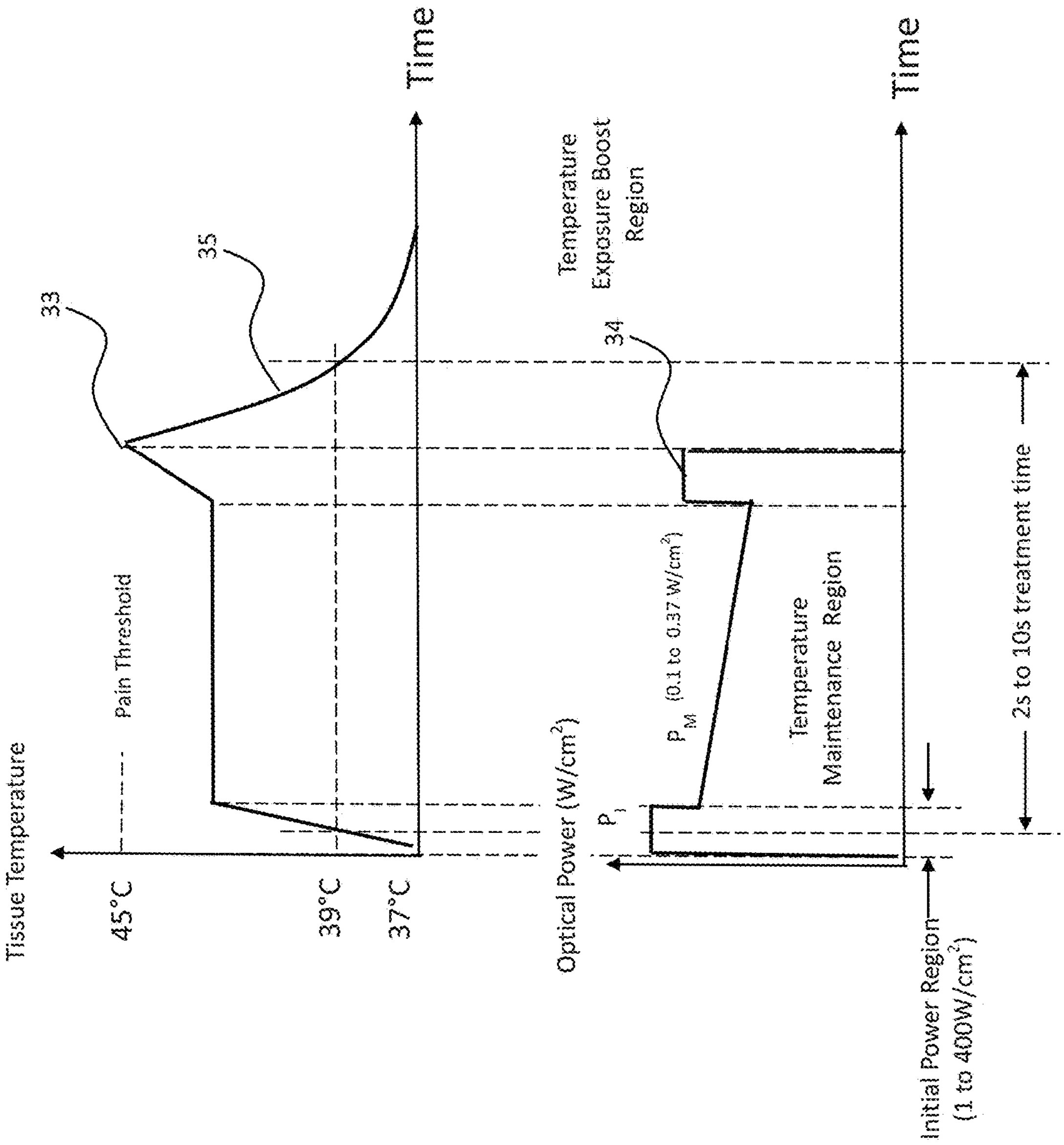
FIG. 8 is a graph illustrating a thermal boost at the end of a treatment pulse, in accordance with embodiments of the present inventive concepts.

The temperature temporal profile of the target tissue can be controlled for predetermined needs by modulating the temporal profile of the optical energy source 8, for example, as described at least at FIGS. 7 and 8. Accordingly, the optical energy source 8 with spatial distribution modification by OSDS 7 can provide therapeutic treatment energies that raise tissue temperature ranging from 2 °C to 8 °C with respect to a current temperature. In an embodiment, the optical energy source 8 provides peak power density requirements ranging from 1 W/cm$^2$ to 400 W/cm$^2$. In an embodiment, the optical energy source provides an average power density to maintain constant tissue temperature, for example, between 0.1 W/cm$^2$ and 0.37 W/cm$^2$. In an embodiment, the operating power density is between 0.1 W/cm$^2$ and 400 W/cm$^2$ The control electronics 9 can control a user interaction and/or energy dosage. The contact sensors 5 and thermal sensor 6 are electrically connected to the control electronics 9. The contact sensor 5 and/or thermal sensor 6 signals are interpreted by the control electronics 9 to determine a contact state and a thermal state, respectively. If the device 1 is in full contact, and the tissue temperature is within acceptable limits, the control electronics permit a laser emission and delivery of electrical current to the optical energy source 8. If the device is not in full contact with the tissue or the tissue temperature is out of acceptable limits, the control electronics 9 will prevent laser emission. Control electronics 9 may include or otherwise communicate with a local microprocessor and embedded control software. The temporal profile of the electrical current delivered to the optical energy source 8 is controlled by the software embedded within the microprocessor. The amount and duration of the electrical current is preprogrammed with the software. The device 1 includes control buttons such as power and treatment buttons as shown in FIG. 2D. User interactions with control buttons are detected by the control electronics 9 and user interface is controlled through the software embedded within the microprocessor. The replenishment cartridges and local computers 64 can communicate with the microprocessor for purposes of treatment usage replenishment and firmware updates, described herein.

The power source 10 may include but not be limited to a power supply circuit and/or a battery that provides a source of electrical energy to the optical energy source 8 and/or other elements of the dermatological medical device 1.

Figure 2A:
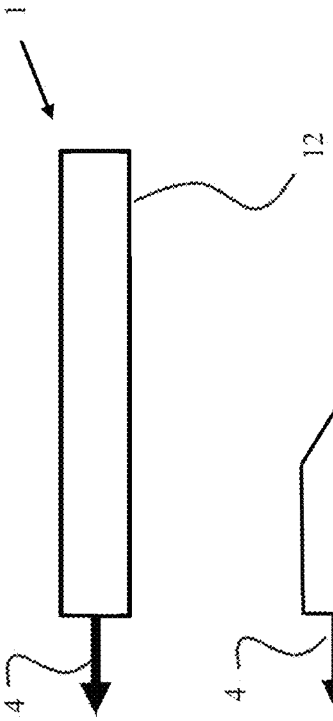
FIGS. 2A-2C are front views of various overall packaging concepts, in accordance with an embodiment of the present inventive concepts.
Figure 2B:
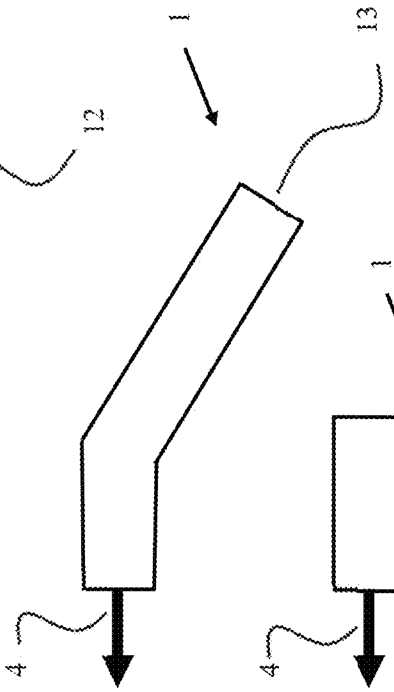
Figure 2C:
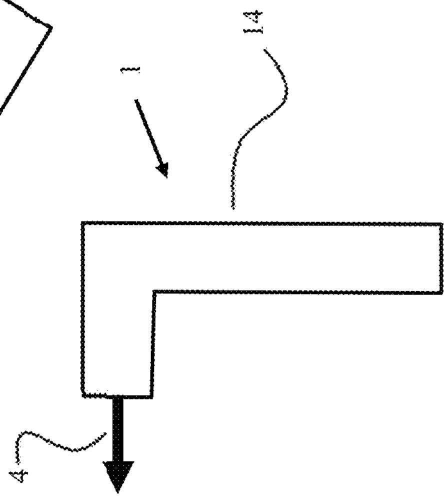
Figure 2D:
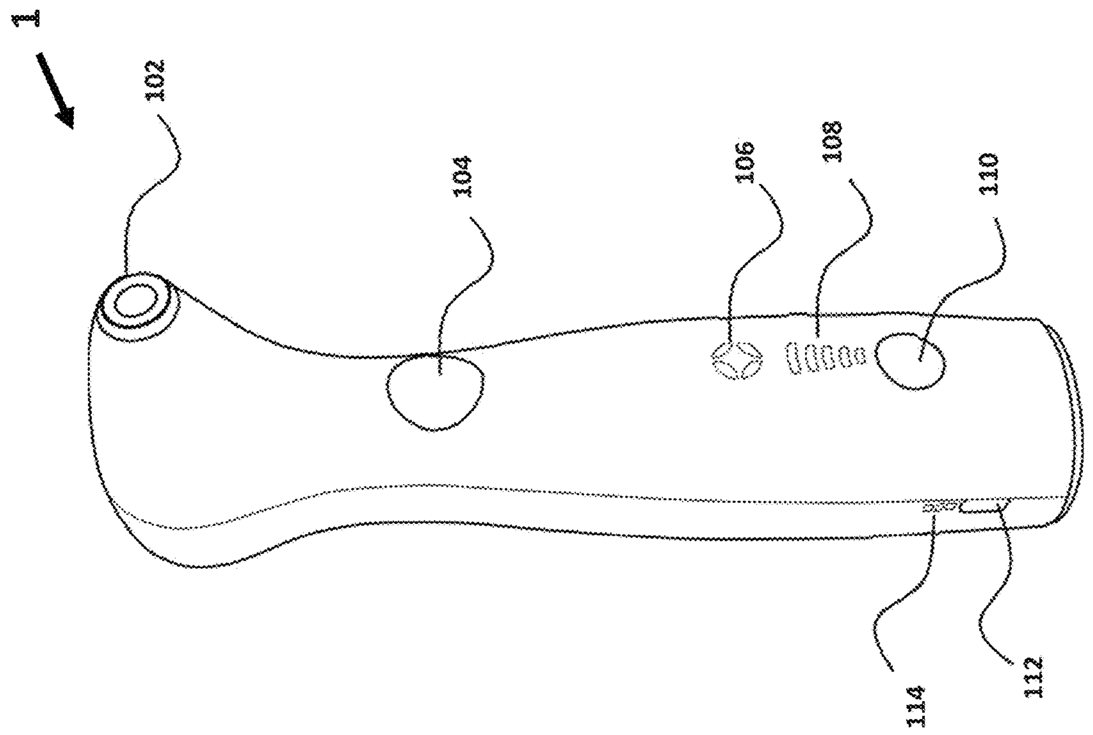
FIG. 2D is a perspective view of a handheld dermatological medical device of FIGS. 1-2C, in accordance with an embodiment of the present inventive concepts.

FIGS. 2A-2C are side views of various overall packaging concepts, in accordance with an embodiment of the present inventive concepts.

One or more subsystems described herein can be packaged in a manner that provides an ergonomically optimized shape and configuration. Also, the enclosure 11 of the handheld dermatological medical device 1 referred to in FIG. 1 may be constructed and arranged for different gripping methods and/or for ergonomic considerations. In one embodiment, as shown in FIG. 2A, the handheld dermatological medical device 1 has a straight cylindrical shape 12. In another embodiment, as shown in FIG. 2C, the handheld dermatological medical device 1 is constructed and arranged so that the distal end is perpendicular to the main body of an enclosure 14. Here, optical energy 4 is output in a direction that is perpendicular to the main body of the enclosure 14. In another embodiment, as shown in FIG. 2B, the optical energy 4 is output in a direction that is angled between 0 and 90° relative to the main body of an enclosure 13. Regardless of the configuration of the enclosure 11, the enclosure 11 permits a complete heat shock therapeutic system solution for a user, e.g., a consumer, that is cost effective with respect to manufacturing and purchasing by a user.

FIG. 2D is a perspective view of a handheld dermatological medical device 1 of FIGS. 1-2C, in accordance with an embodiment of the present inventive concepts.

The device 1 includes one or more of a safety sensor 102, a treatment button 104, a replenishment indicator 106, a power setting indicator 108, a power button 110, a device connector 112, and a battery indicator 114.

The safety sensor 102 can include the contact sensor 5 and/or thermal sensor 6 described herein and can be positioned at or proximal to a treatment area.

The treatment button 104 can be constructed and arranged to activate or inactivate the device 1, for example, to control a treatment operation performed at a treatment area.

The replenishment indicator 106 can display information, a light, or other indicator regarding an amount of time, uses, or the like that is remaining at the device 1. For example, the indicator 106 can include four regions, each corresponding to 25% of available replenishment capacity of the device 1.

When one region is illuminated during operation, for example, by an LED, this can indicate that the device 1 is approaching an end of a current replenishment cycle. When the device 1 receives a replenishment-related signal (described below), additional regions at the indicator 106 can be illuminated during operation.

The power setting indicator 108 can display information, light, or other indicator regarding a power setting, for example, indicative of an amount of optical energy 4 that is output from the device 1. The power button 110 is constructed for a user to activate and inactivate the device 1. When the power button 110 is activated, one or more of the indicators 106, 108, and 114 can illuminate or display information and the treatment button 104 can be pressed to establish an operation of the device 1.

The device connector 112 can be coupled to a USB device, a charger, and/or other external device for exchanging electrical signals, power, data, electrical signals, and so on.

The battery indicator 114 can display information, light, or other indicator regarding a power condition of the device 1. For example, the battery indicator 114 can display an amount of battery life left in the device 1. The battery indicator 114 can include multiple regions, similar to the replenishment indicator 106, except that the regions of the power setting indicator 108 pertain to an amount of remaining power. Alternatively, the indicator 114 can illuminate or otherwise display information indicating that the device 1 is receiving power from an external power source, e.g., a wall socket.

Figure 3B:
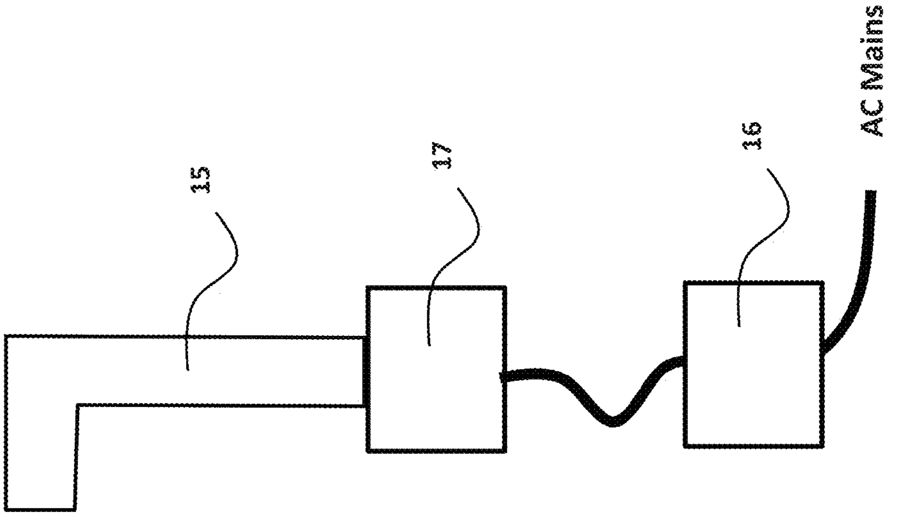
FIGS. 3A and 3B are block diagrams of a handheld dermatological medical device, in accordance with another embodiment of the present inventive concepts.
Figure 3A:
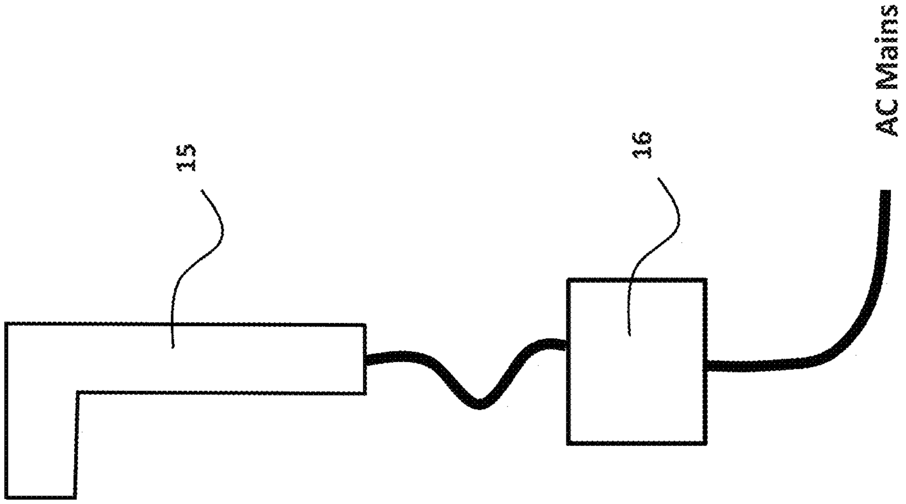

FIGS. 3A and 3B are block diagrams of a handheld dermatological medical device 15, in accordance with another embodiment of the present inventive concepts. The device 15 can be similar to or the same as those described with reference to FIGS. 1 and 2. Therefore, details of the device 15 are not repeated for brevity.

In FIG. 3A, the device 15 may be electrically powered by connecting a low voltage power supply 16 directly to the device 15. The power supply 16 can be coupled to a power source, such as an AC power receptacle. Alternatively, the power supply 16 can include a power source such as a battery. The power supply 16 can direct power to elements of the device 15 such as an optical energy source similar to the optical energy source 8 described with respect to FIG. 1, in which case the device 15 would require power via a power connector. The power connector is preferably coupled to a proximal end of the device 15 opposite a distal end where optical energy is output. Power supply 16 may also be a local computer providing low voltage electrical power to the device 15, as an example through a USB port.

In FIG. 3B, the device 15 is electrically charged at a charging dock station 17, which in turn receives power from a power supply 16. Accordingly, the device 15 in FIGS. 3A and 3B can be electrical charged by direct contact or inductive charging methods well known to those of ordinary skill in the art.

Figure 4:
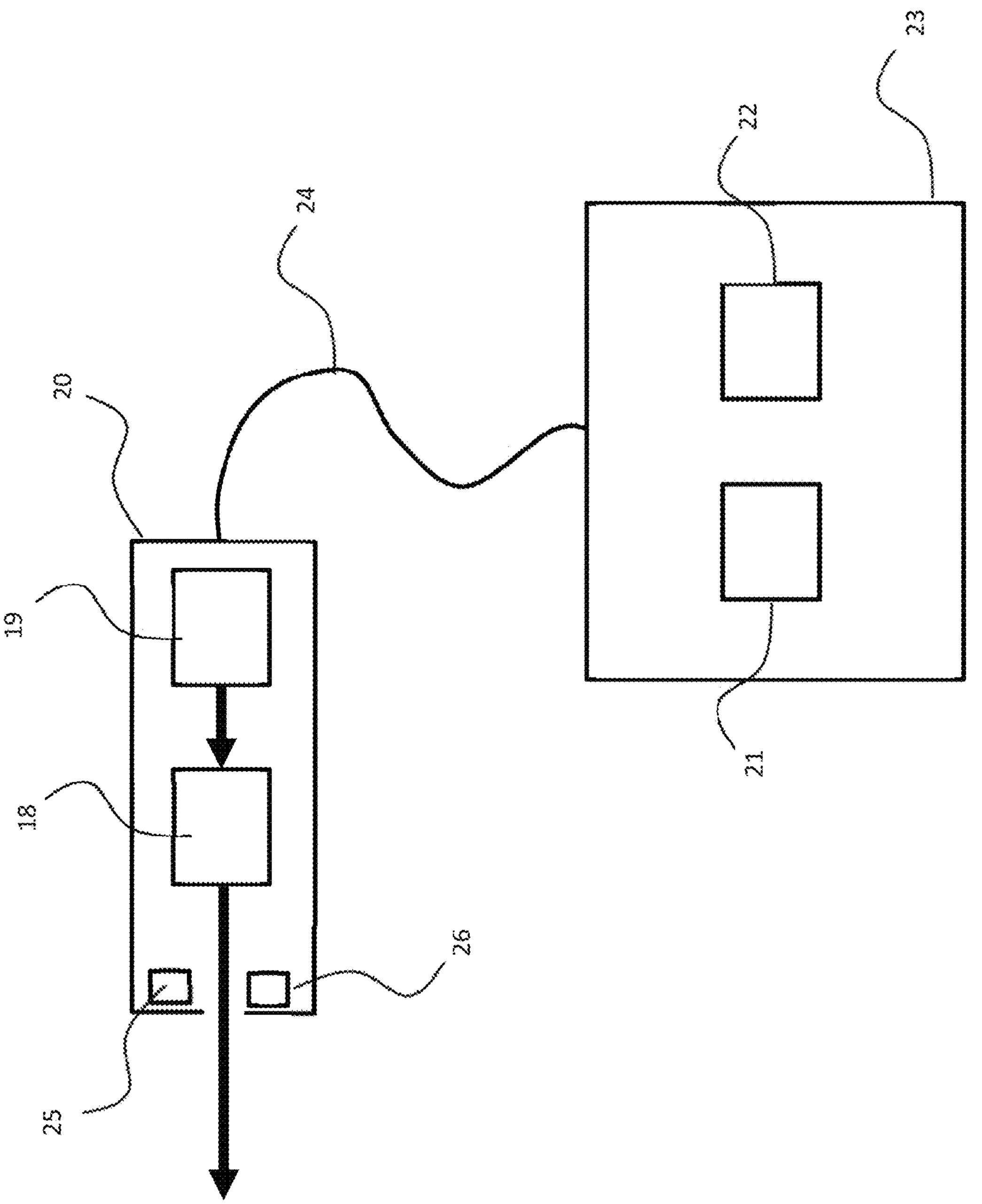
FIG. 4 is a block diagram of a handheld dermatological medical device packaged separately from control electronics and a power source, in accordance with another embodiment of the present inventive concepts.

FIG. 4 is a block diagram of a handheld dermatological medical device 20 packaged separately from control electronics and a power source, in accordance with another embodiment of the present inventive concepts.

As illustrated in FIG. 4, the handheld dermatological medical device 20 can include a contact sensor 25, a thermal sensor 26, an OSDS 18 and an optical energy source 19, which are packaged under a common housing. The contact sensor 25, thermal sensor 26, OSDS 18 and optical energy source 19 can be similar or the same as those described herein, and therefore details are not repeated for brevity. In FIG. 4, the handheld dermatological medical device 20 is separate from a set of control electronics 21 and a power source 22, which can be packaged in a separate enclosure, referred to as a console housing 23, or other device that is remote from the handheld dermatological medical device 20. An electrical cable 24 can extend from the console 23 and can be coupled to the handheld device 20 to deliver electrical power to the device 20, and to provide electrical communications with the device 20. The interactions between the contact sensor 25, thermal sensor 26, OSDS 18, optical energy source 19, control electronics 21 and power source 22 can be similar or the same as those described at least at FIG. 1, and therefore details are not repeated for brevity. The handheld dermatological device 20 may be disconnected from the console housing 23 for purposes of new handheld device connections or replacements. Different OSDS 18 and optical energy sources 19 with different optical operating parameters such as spatial distribution, optical power, and wavelengths may be easily connected to a common console housing 23.

Figure 5:
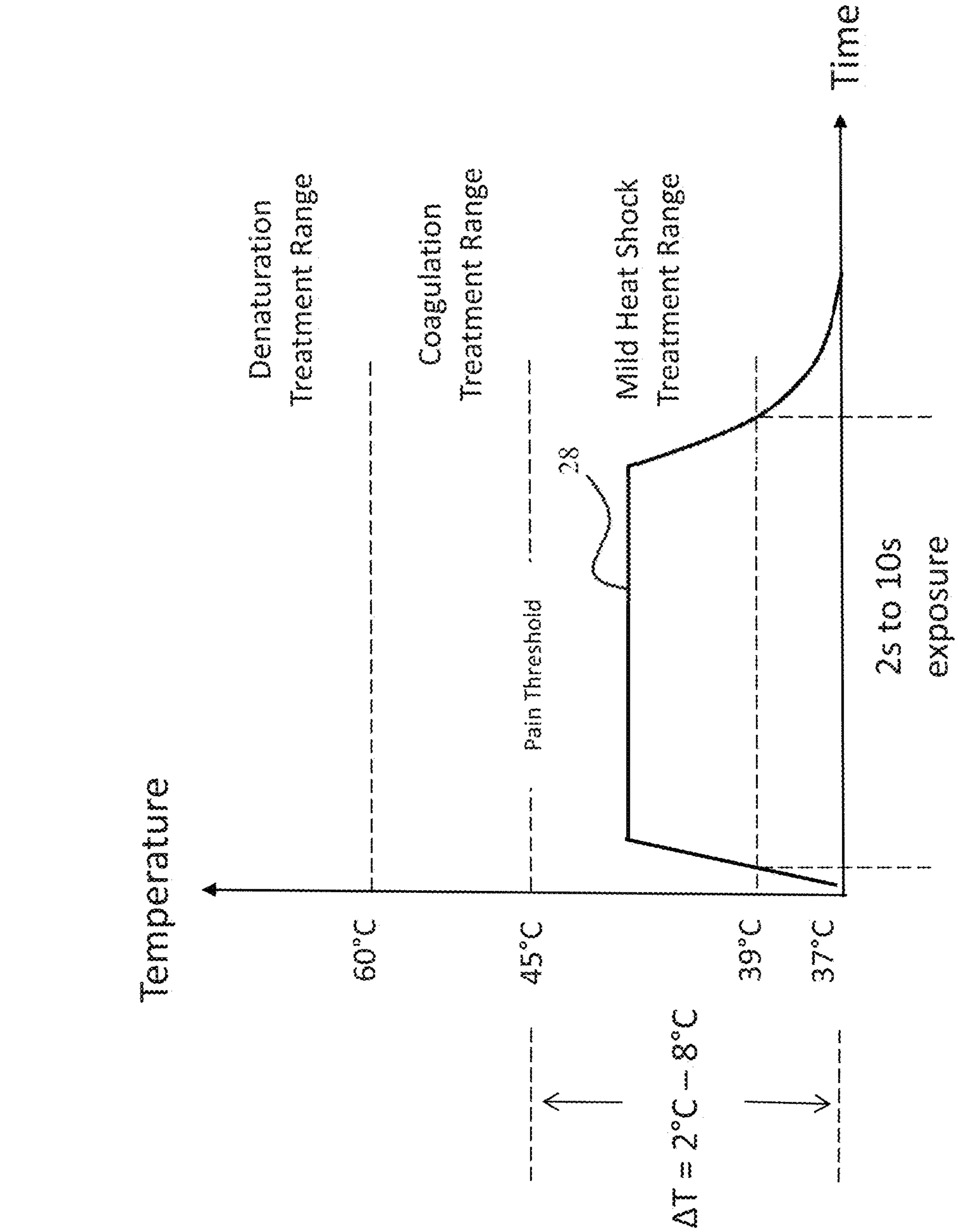
FIG. 5 is a graph illustrating a temperature range of a treatment, in accordance with embodiments of the present inventive concepts.

FIG. 5 is a graph illustrating a temperature range of an example medical treatment, consistent with embodiments of the present inventive concepts. The medical treatment can include a dermatological procedure known to those of ordinary skill in the art, for example, wrinkle removal or reduction.

In some embodiments, as described herein, HSP formation occurs when a temperature of human or animal tissue is increased by 2 °C or more. As also described herein, therapeutic goals are to generate non-injurying temperature increases in tissue with minimal or no pain. Conventional non-ablative therapies include thermal denaturization which occurs at temperatures at or exceeding 60 °C, and thermal coagulation which occurs at temperatures at or exceeding 45 °C. Hence, a goal for treatments performed in accordance with the present inventive concepts can occur by increasing a body target tissue temperature by 2 °C to 8 °C without exceeding a temperature of 45 °C at which pain is typically experienced. In this manner, a treatment can be performed in a mild heat shock treatment range, for example, between 37 °C to 45 °C, shown in the desired treatment range 28.

To maximize the therapeutic efficacy and minimize unintended side effects, embodiments of the present inventive concepts provide systems and methods for controlling the amount of therapeutic energy delivered at target tissue, by controlling the temporal profile of energy, for example, laser energy, delivered to a tissue region undergoing a treatment. Both peak powers and exposure time of the energy output from a dermatological medical device can be modulated to provide a desired clinical effect.

Also, as shown in FIG. 5, in some embodiments, an exposure of energy output from a dermatological medical device that is between 2-10 seconds at temperatures that do not exceed 45 °C is preferable for treatment. Tissue that is exposed to an elevated temperature for more than 2 seconds can result in an up-regulation of HSPs, or an increased expression of one or more genes corresponding to tissue cells, and as a result, the proteins, more specifically HSPs, encoded by those genes. However, heat shock exposure at least at 45 °C for more than 10 seconds can have a traumatizing effect on cell proliferation.

Accordingly, in an embodiment, a desirable HSP expression occurs when tissue is exposed to a >2 °C temperature increase for an exposure duration of 2-10 seconds of exposure.

Figure 6:
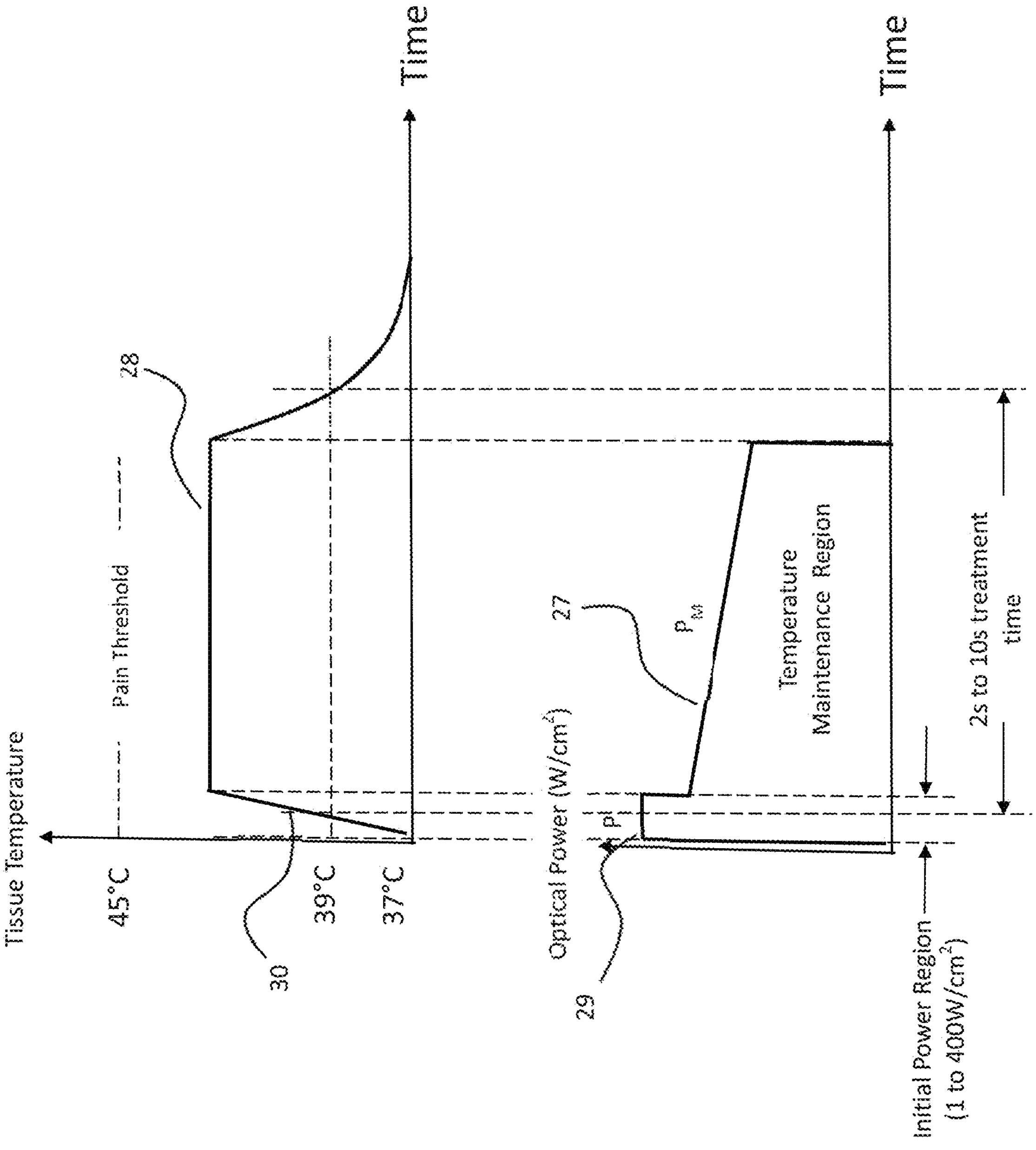
FIG. 6 is a graph illustrating a skin temperature temporal profile relative to an optical power continuous wave temporal profile, in accordance with embodiments of the present inventive concepts.

FIG. 6 is a graph illustrating a skin temperature temporal profile relative to an optical power continuous wave temporal profile, in accordance with embodiments of the present inventive concepts. The skin temperature temporal profile can be similar to or the same as that shown at FIG. 5.

An optical power amplitude can be modulated during a treatment pulse to generate the desired temporal temperature profile as shown in the optical power continuous wave temporal profile of FIG. 6. Consideration can be made to deliver high power 29(P) at the beginning of the pulse to maximize a temperature rise rate 30 shown at graph illustrating the skin temperature temporal profile. As an example, experimental data has shown that 1 $W/cm^2$ provides a temperature rise rate of approximately 1 °C/s at 0.5 mm tissue depth. Pulsewidths of 20 ms or longer are required to stay below ablative parameters. For temperature rise rate 30 required to increase tissue temperature by 8 °C within 20 ms may require a peak power density of 400 $W/cm^2$. A treatment spot size delivered by the OSDS 7 will be sized according to optical output power capabilities of the optical energy source 8. A 1 mm diameter treatment spot is able to achieve 400 $W/cm^2$ with an optical energy source 8 capable of producing 3.14 W. Alternatively, the minimum temperature rise rate 30 with a temperature rise of at least 2 °C within 2 s may require 1 $W/cm^2$. The power 27 can be reduced at region $P_M$, referred to as a temperature maintenance region, to maintain the temperature within a desired treatment range 28 shown at the graph illustrating the skin temperature temporal profile, preferably below a pain threshold at or about 45 °C as shown in the temporal temperature profile graph.

The pulse shape is shown in FIG. 6 as a continuous waveform. In other embodiments, different pulse structures can equally apply. For example, as shown in FIG. 7, the pulse amplitude and temporal structure can be modulated to achieve desired target temperature profile. A temperature amplitude 31 can be modulated as a result of the pulse structure 32. The control electronics 9 can provide a modulated electrical current to the optical energy source 8, resulting in pulse structure 32.

As described above, embodiments of the present inventive concepts include a device that provides a noninjuring heat shock treatment, wherein the minimum target tissue temperature increase is between 2 °C-8 °C, and remains below the pain threshold of or about 45 °C. In an embodiment, the treatment dosage is provided by an optical energy source, for example, controlled by the control electronics 9, 21 described herein and output by the optical energy source 8, 19 described herein.

Figure 26:
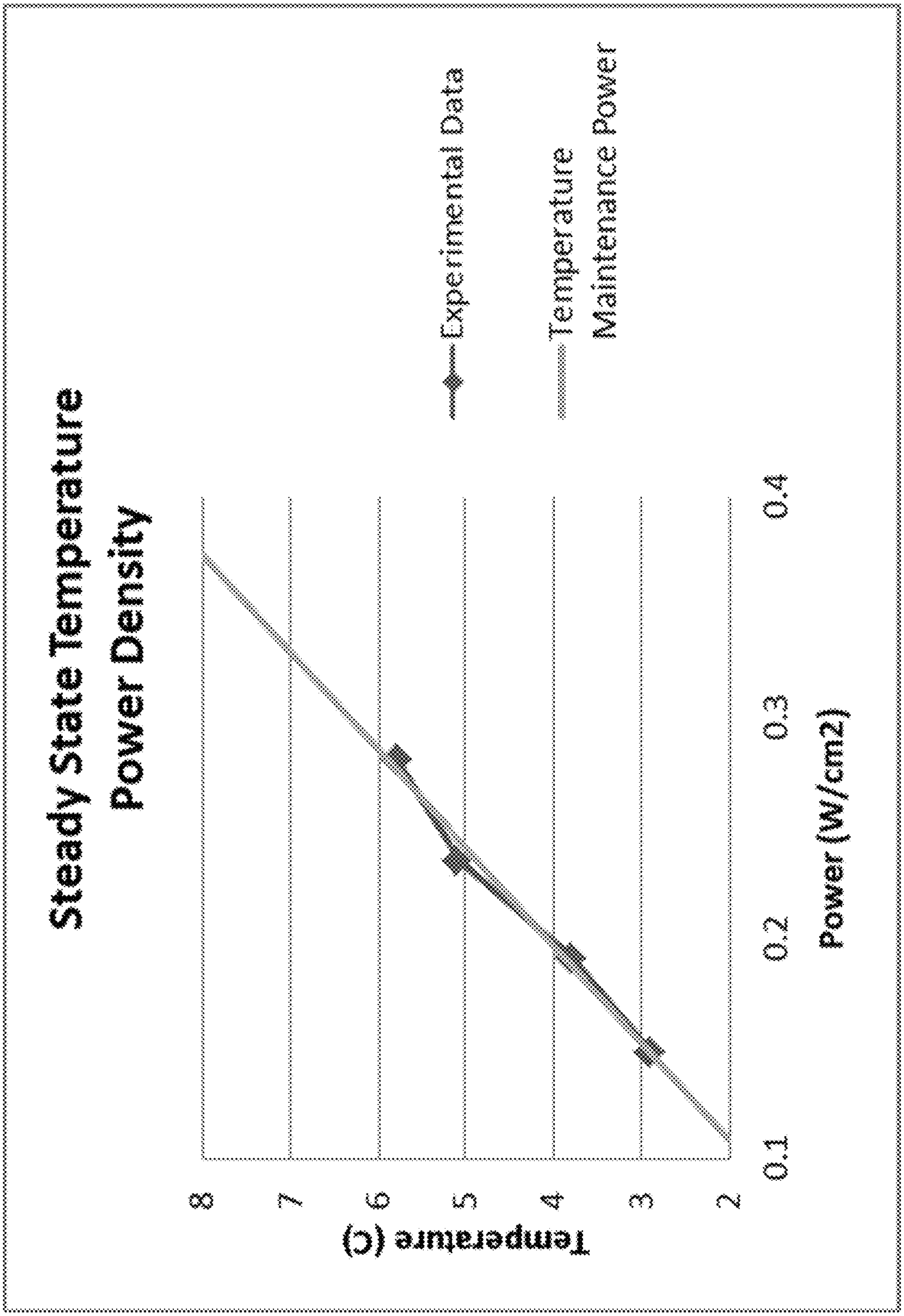
FIG. 26 is a graph illustrating power deliveries required to maintain a desired steady state temperature rise, in accordance with some embodiments.

Experimental data shows that at 6.8 $W/cm^2$ power density can generate a 6.8 °C/s temperature rise in live human tissue at a 0.5 mm depth. Experimental data also indicates a resulting temperature rise rate of 1 °C/s per 1 $W/cm^2$ at the 0.5 mm tissue depth. In an embodiment, a treatment pulse width is less than 2 seconds. In a non-ablative therapy according to some embodiments, pulse widths are generally equal to or greater than a few milliseconds. In some embodiments, a pulse width ranges from 0.02 to 2 seconds. Required peak power density range is 1 $W/cm^2$ to 400 $W/cm^2$. Further empirical data has shown that 0.1 $W/cm^2$ is required to maintain a steady state temperature rise of 2 °C and 0.37 $W/cm^2$ for maintaining a steady state temperature rise of 8 °C, for example, shown at FIG. 26.

In an embodiment, an HSP expression is dependent on temperature exposure and/or time duration exposure times. As therapeutic energy and time exposure requirements increase, the system performance requirements can increase, thus increasing size and cost of the product. In an embodiment, provided are a system and method that extend the thermal exposure time by providing a thermal boost at the end of the treatment pulse.

Figure 27:
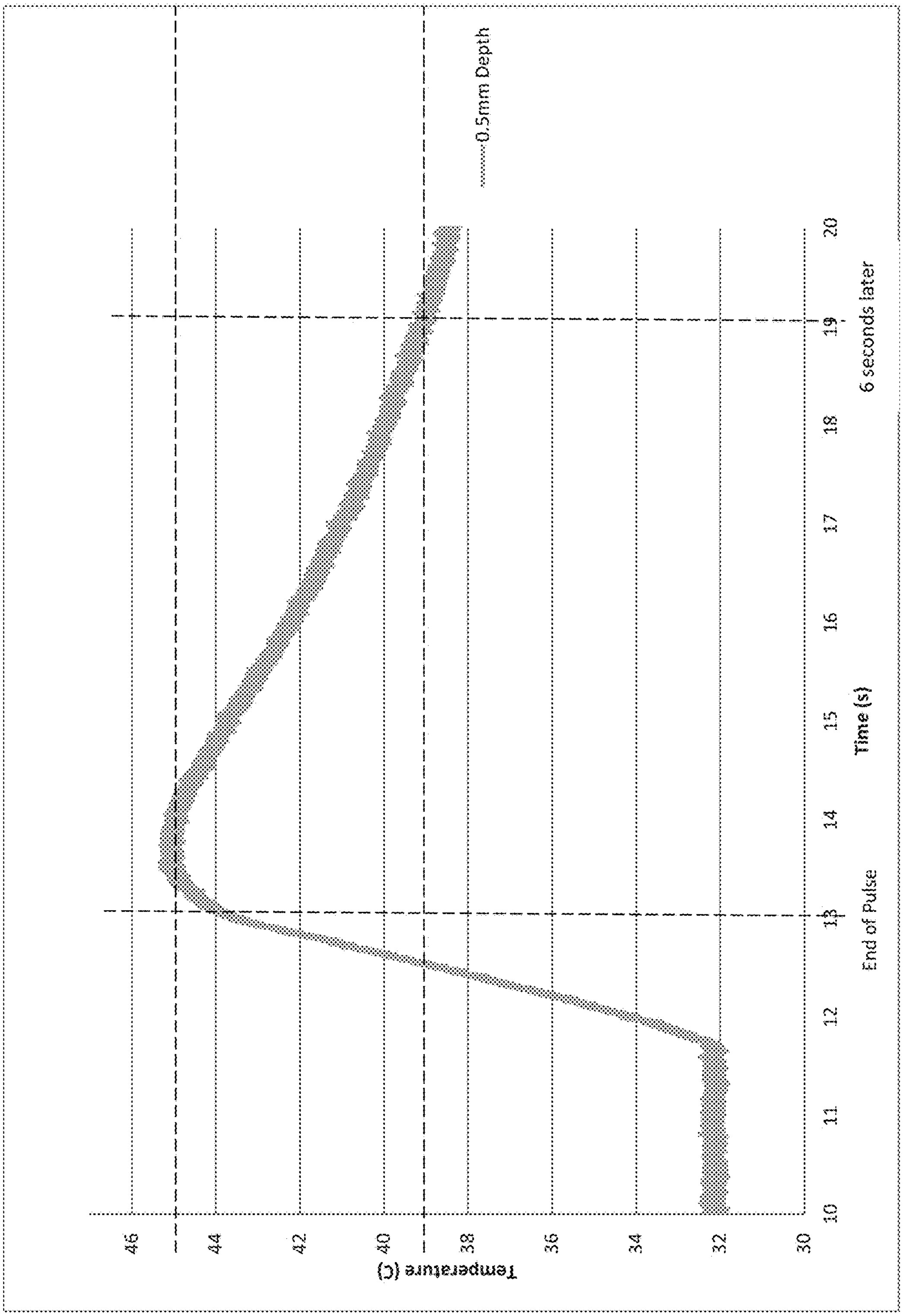
FIG. 27 is a graph illustrating a thermal boost time in live human tissue, in accordance with some embodiments.

FIG. 8 is a graph illustrating a thermal boost 33 at the end of a treatment pulse, in accordance with embodiments of the present inventive concepts. The thermal boost 33 is produced by an increase of output power from the optical energy source 8 as a result of increased electrical current produced from the control electronics 9. The temporal structure of a generated treatment pulse 34 may be modified to provide an additional boost of power at the end of the pulse to extend the exposure time 35 of the tissue to elevated therapeutic treatment temperatures, preferably not greater than the pain threshold temperature of or about 45 °C. A thermal boost at or near the end of the treatment pulse may minimize pain while maximizing temperature exposure time and HSP generation. Experimental results in human testing have demonstrated an extended temperature exposure time of 6 seconds before cooling below a therapeutic temperature threshold, for example, illustrated at FIG. 27.

Laser light propagation through the skin depends on the optical properties of the skin and the laser light wavelength. In doing so, the device can be constructed and arranged so that the spatial distribution determines the effectiveness of reaching target tissue depths. Laser non-ablative stimulation of collagen synthesis typically ranges from a 676 nm to 1540 nm region, but is not limited thereto. The device can also be constructed and arranged such that wavelength selection is optimized for an efficient conversion of light energy to heat at the intended treatment region.

Figure 9:
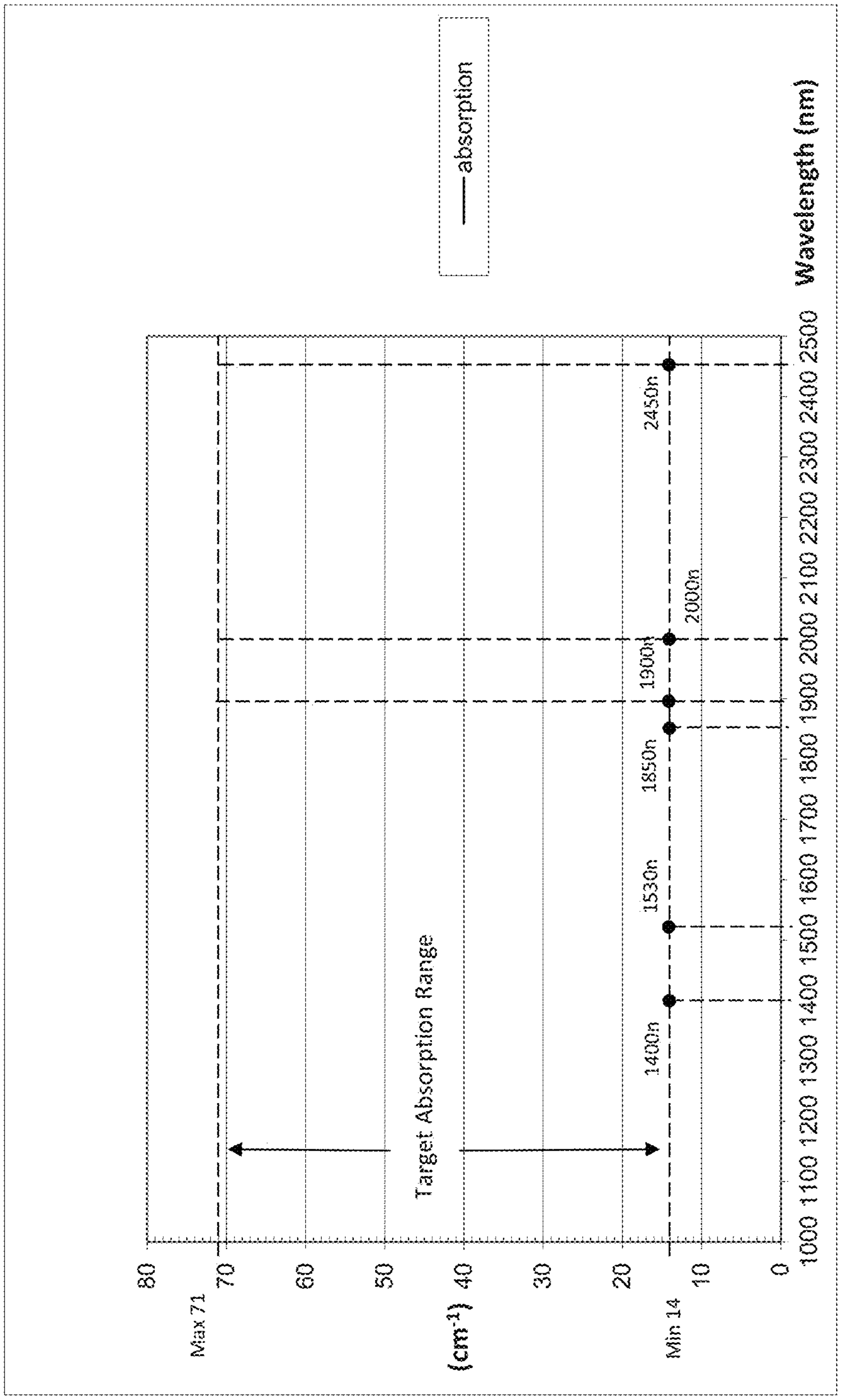
FIG. 9 is a graph illustrating a set of wavelength ranges of interest, in accordance with embodiments of the present inventive concepts.

FIG. 9 is a graph illustrating a set of wavelength ranges of interest, in accordance with embodiments of the present inventive concepts. An optical energy source of a handheld dermatological medical device, for example, described at FIGS. 1-4, can generate electromagnetic energy at one or more of the wavelengths as shown in FIG. 9. Lasers can be provided that generate light at a wavelength within a narrow spectral bandwidth. Lamps can be provided that generate broader spectral bandwidths.

In an embodiment, a target therapeutic region of tissue of interest is at least ⅓ of an average dermis thickness of 3 mm. With regard to skin, water is the predominant chromophore of absorption. Thus, targeting water as a most effective absorptive chromophore while ensuring that energy is delivered to a target region can be economically effective. Selecting an operating wavelength that is not at the peak absorption of water may be on orders of magnitude poorer absorption, resulting in little to no effect. In this case, the amount of energy delivered to the tissue must be increased on an order of magnitude sufficient to reach equivalent effectiveness. This requires an increased power output from the optical energy source 8, which in turn requires an increased power delivery from the control electronics 9. If such increases are technically feasible, manufacturing costs make the device economically ineffective.

A first order approximation can be determined by using the attenuation formula (1). The purpose of the formula is to determine the desired operating wavelengths.

$$I=I_0 e^{-(\eta\alpha x)} \quad (1)$$

Where:

x=distance

η=concentration percentage of absorption

=absorption coefficient

I=intensity at distance x $I_0$=initial intensity

It follows that α can be determined with a known intensity ratio ($I/I_0$) and required depth x. In an embodiment, the absorption length is determined to be between 0.2 mm, which is beyond the epidermal layer and 1 mm at 37% intensity level. An absorption length is distance (x). In an embodiment, the required resulting total absorption coefficient is between 14 $cm^{-1}$ and 71 $cm^{-1}$. As shown in FIG. 9, wavelength ranges of interest can include but not be limited to 1400 nm-1530 nm, 1850 nm-1900 nm, and 2000 nm-2450 nm.

In some embodiments, the energy source, for example, the optical energy source 8 or 19 referred to herein, is a narrowband or monochromatic laser source emitting in one or more of the wavelength bands of interest. In some embodiments, the energy source is a narrowband light emitting diode (LED) or the like. In another embodiment, the energy source is a broadband emitting lamp or filament bulb emitting near infrared broadband, for example, providing wavelength bands of 1400 nm to 1900 nm and 2000 nm to 2450 nm.

The effective delivery of therapeutic light energy to the target depth can directly affect the efficacy of the treatment. The reduction of a preliminary energy loss by reducing or removing absorbing chromophore in the stratum corneum of the skin is described herein. Another potential form of energy loss can occur due to the mechanical distance of the target treatment region from the source Conventional doctor-prescribed and consumer devices alike provide injurying treatment dosages to the tissue. Accordingly, side effects such as significant pain and extended healing times are prevalent. Also, frequent usage, for example, daily applications, is prohibited for doctor-prescribed treatment modalities. As technology and commercialization costs decline, laser based treatment modalities are becoming readily available to the consumer market. However, market acceptance is limited by the cost of treatments and the abovementioned side effects. An HSP expression can increase over time and then returns to normal levels, with peaks occurring between 1.5 and 48 hours. Furthermore, a maximum up-regulation of both procollagen types I and III gene expressions can occur at or about 24 hours after heat shock exposure.

In a preferred embodiment, a non-injurying heat shock treatment is performed a handheld dermatological medical device on a predetermined basis, for example, a daily or an hourly treatment regimen.

Figures 10A, 10B:
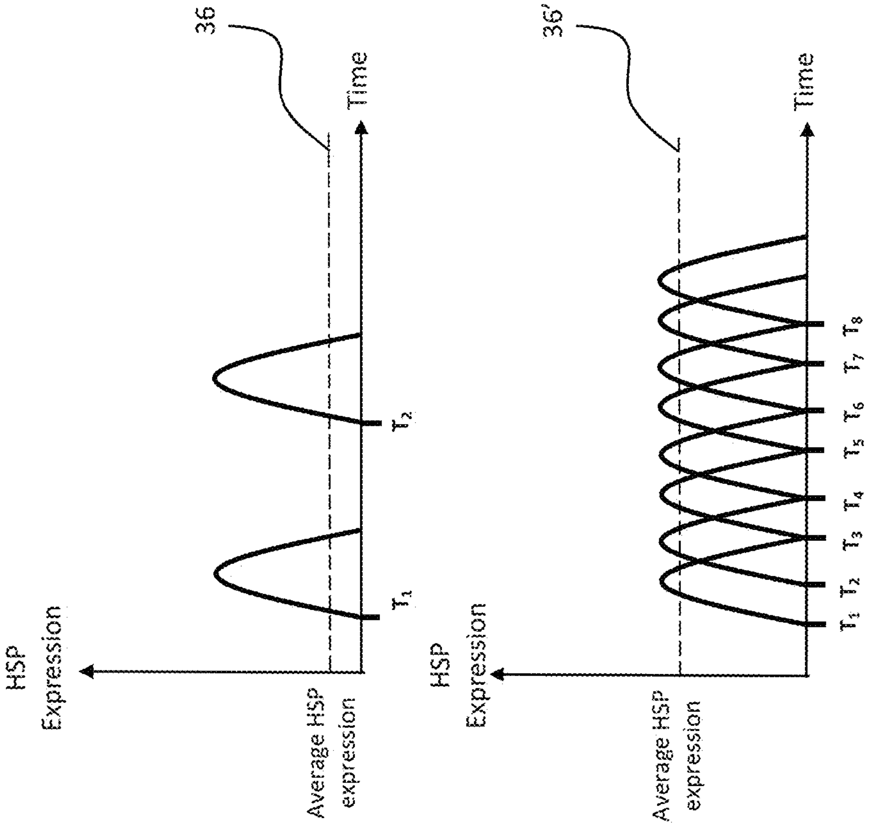
FIGS. 10A and 10B are graphs illustrating an average heat shock protein (HSP) expression relative to treatment intervals, in accordance with embodiments of the present inventive concepts.

FIGS. 10A and 10B are graphs illustrating an HSP expression over time relative to treatment intervals, in accordance with embodiments of the present inventive concepts.

In FIG. 10A, first and second heat shock treatments are provided on a tissue region. The first heat shock treatment occurs at a first time $T_1$. The second shock treatment occurs at a second time $T_2$, or a predetermined period of time after the first time $T_1$. As an example, HSP expression will start and peak sometime between 1.5 hours to 48 hours after treatment T1. If the second treatment $T_2$ is delayed for 1 week after $T_1$, the treated tissue may be without any HSP expression for as long as 5 to 7 days, minimizing collagen synthesis.

As illustrated in FIG. 10B, the time between treatments, e.g., $T_1$ and $T_2$, of a plurality of treatments ($T_1$-$T_8$) can be significantly reduced. In doing so, an average HSP expression 36 can be increased to an average HSP expression 36'. An HSP expression, i.e., an amount, increases and peaks over time after treatment. The "average HSP expression" is the average amount of HSP produced during the period of time. As a treatment frequency increases, the average procollagen type 1 and HSP expression increases resulting in more collagen synthesis. Accordingly, the systems and methods in accordance with embodiments can provide cost effective and efficacious daily or even hourly treatments. Conventional doctor-prescribed treatments, on the other hand, can be cost prohibitive for daily treatments.

Figure 11:
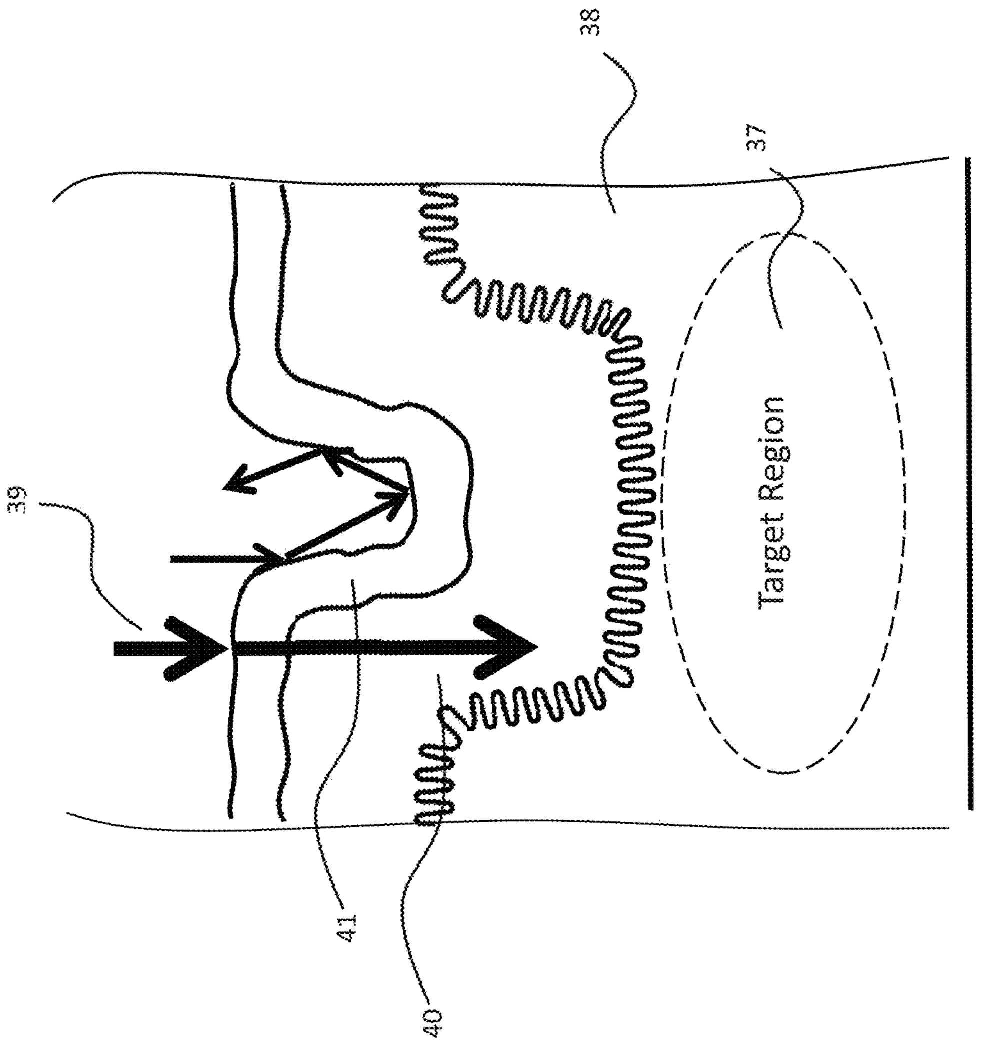
FIG. 11 is a view of the geometry of a skin wrinkle.

FIG. 11 is a view of the geometry of a skin wrinkle 38. Animal or human skin includes three main layers: a stratum corneum 41, an epidermis 40, and a dermis 37, as is well-known to those of ordinary skill in the art. Depending on the body location, the thickness of the stratum corneum layer 37 can be from 10 to 20 μm. The epidermis layer 40 can have a thickness from 50 to 150 μm. The dermis layer 37 can have a thickness ranging from 300 μm to 3 mm.

Water content in the stratum corneum 41 can range from 15% at the outer surface to 40% at a junction of stratum corneum 41 and the epidermis 40. Further into the epidermis 40, the water content can quickly increase 70%, where saturation may occur. In an embodiment, water is a main chromophore. Reducing the chromophore in the stratum corneum 41 reduces energy absorption at the stratum corneum 41, resulting in less heat generation. Reducing heat absorption in the stratum corneum 41 also reduces pain since free nerve endings end at the junction of the stratum corneum 41 and epidermis 40. In a preferred embodiment, a dessecating aqueous solution is used as part of a treatment protocol to remove surface tissue moisture, and thus reducing a loss of laser energy generated by a handheld dermatological medical device at the surface of the skin.

Figure 12:
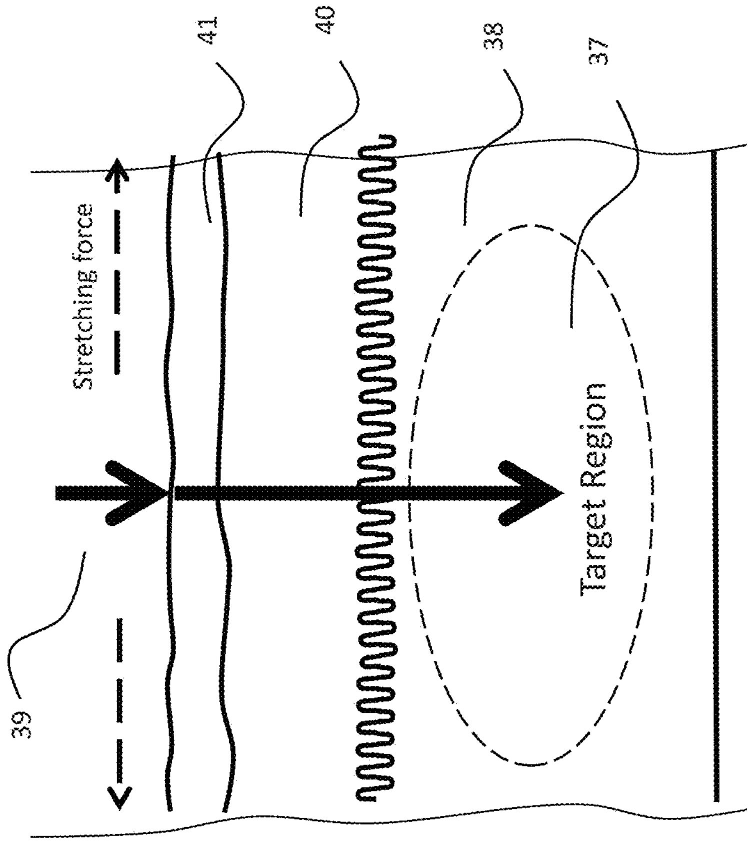
FIG. 12 is a view of a skin wrinkle that is stretched, in accordance with embodiments of the present inventive concepts.

The folds in the stratum corneum 41, the epidermis 40, and the dermis 37 illustrate the presence of a wrinkle. The geometry of the wrinkle 38 may prevent a delivery of electromagnetic radiation such as light 39 output from a handheld dermatological medical device to a targeted region in the dermis 37. The light 39 can propagate further along the folded epidermis 40 and/or the stratum corneum 41. As shown in FIG. 12, a mechanical manipulation of the wrinkle to flatten or stretch the tissue can allow an effective delivery of the light 39 or other electromagnetic radiation may be achieved by manually stretching the skin or feature may be built into a device such as the handheld device described in accordance with embodiments herein. Stretching the skin in this manner can permit laser light or the like output from the device to propagate deeper into the tissue by reducing the optical path length. Stretching the skin in this manner can also thin the tissue, thereby forcing additional chromophores such as water and blood away from the treatment site.

Figure 13:
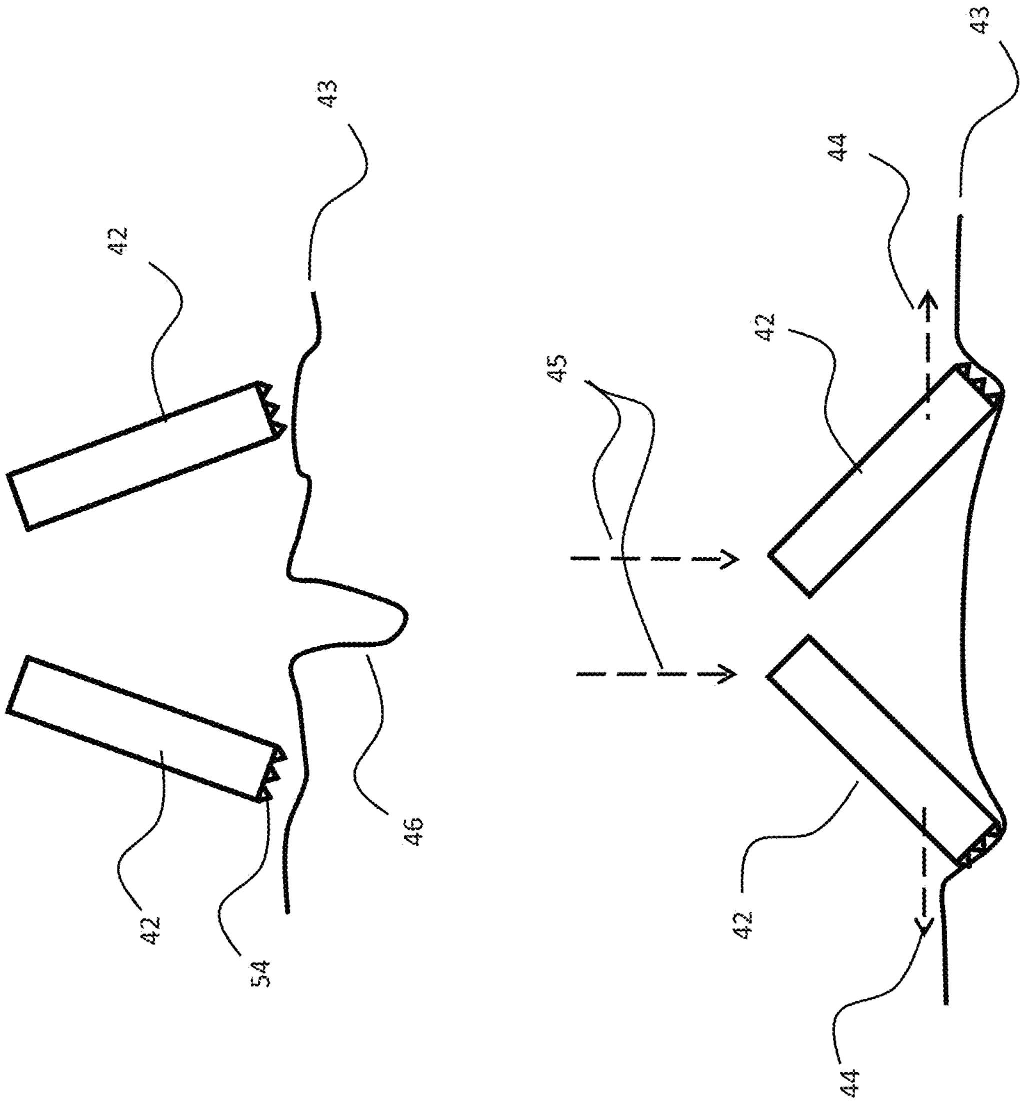
FIG. 13 is a view of a skin stretching mechanism applied to a skin wrinkle, in accordance with embodiments of the present inventive concepts.

FIG. 13 is a two-dimensional cross section view of a skin stretching mechanism 42 applied to a skin wrinkle, in accordance with embodiments of the present inventive concepts. The skin stretching mechanism 42 can include two or more elements that are separate from, and move independently of each other. The elements of the skin stretching mechanism 42 can be movably coupled to a handheld dermatological medical device, for example, coupled to and pivoting about the treatment end of the enclosure 11 of the device 1 described with reference to FIG. 1, or the device 53 described with reference to FIG. 15. The concept can be expanded to a three-dimensional solution, where the device stretches the skin tissue 43 in multiple axial directions. The mechanism 42 can apply a mechanical cam action to stretch the skin tissue 43. Friction at the tip 54 of the mechanical stretching mechanism 42 may be increased through texturing.

In a preferred embodiment, the skin stretching mechanism 42 stretches the tissue 43 with outward forces 44, also referred to as stretching forces, when a downward force 45 is applied, temporarily reducing or removing the wrinkle 46. Here, each of the elements 42 moves in opposite directions with respect to each other to stretch the tissue 43. For example, as shown in FIG. 13, the leftmost element 42 can move in a first linear direction along an axis, and the rightmost element 42 can move in a second linear direction opposite the first linear direction along the same axis.

Figure 14:
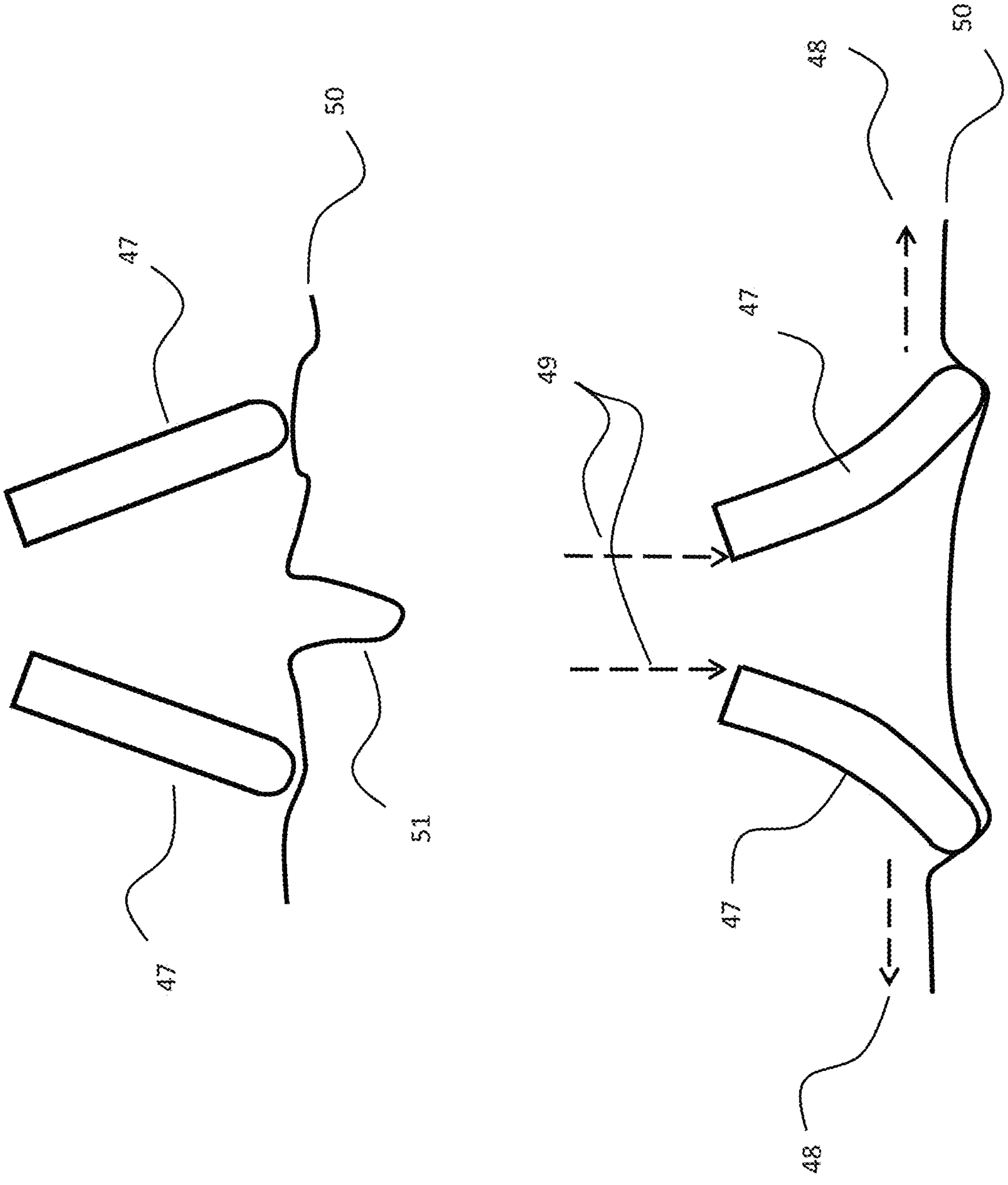
FIG. 14 is a view of a polymer realization of a skin stretching mechanism, in accordance with embodiments of the present inventive concepts.

FIG. 14 illustrates a skin stretching mechanism 47 including a pliable polymer material. In a preferred embodiment, two or more elements of the skin stretcher mechanism 47 can stretch the tissue 50 with outward forces 48 when a downward force 49 is applied, reducing or removing a wrinkle 51, in particular, when a stretching action is performed on the tissue 50 in combination with an application of optical energy from the device in accordance with an embodiment, for example, described herein.

Figure 15:
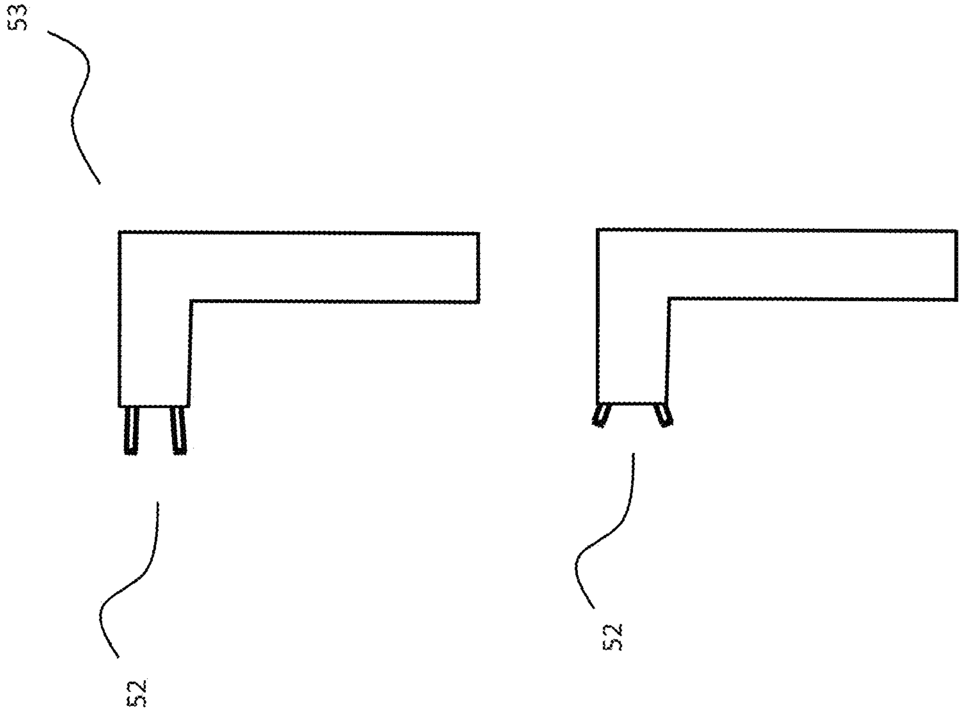
FIG. 15 is a view of a mechanical skin stretching mechanism integrated into a handheld

FIG. 15 is a view of a mechanical skin stretching mechanism 52 integrated into a handheld dermatological medical device 53, in accordance with an embodiment of the present inventive concepts. For example, as described above, elements of the stretching mechanism 52 can be movably coupled to the device 52 so that the elements 52 can pivot, rotate, extend, or otherwise move relative to each other during a skin stretching operation, for example, when a force is applied by the device 53 to target issue, thereby causing the elements to move in directions different from each other, thereby stretching the target tissue, temporarily removing a wrinkle to reduce the optical path length to the target tissue.

The target consumer for the beauty market typically has a routine beauty regime, and is willing to undergo the ongoing expense to maintain this regime. The typical buying habit of the consumer is to purchase beauty products on a periodic basis, for example, weekly or monthly. The purchase price of conventional aesthetic laser devices is typically higher than the average consumer can afford or willing to pay, and subsequently, the price barrier often results in a lack of widespread market acceptance, i.e., beauty-conscious consumers. Although the consumer's total annual expenditures may equal or exceed the retail price of an expensive laser device, consumers are less likely to purchase and pay all at once.

Accordingly, some embodiments include a business model that allows the retail pricing level to fit within the target consumer's monthly spending habits. One solution is to spread the consumer's total cost over time instead of incurring it all at once. Some embodiments include a method that spreads the consumer's cost by adopting a replenishment business model.

Consumable items such as topicals are ideal candidates for a replenishment model in that such products are consumed on use. Once the topical is completely consumed, the consumer has to purchase additional quantities of the topical to continue use. Single or limited use disposables also fit within the replenishment business model. As an example, single use disposables, for example, needles, latex gloves, and so on, are used in surgical and medical applications where sterility is a critical concern. Other consumable examples include limited life components such as batteries, light bulbs, and so on. A well-known example is that of the "razor", where a user purchases a single razor, which is constructed and arranged to receive a disposable razor blade. Consumers can therefore purchase relatively inexpensive razor blades on an as-needed basis, which can be coupled to the razor.

Along these lines, some embodiments of the present inventive concepts utilize a replenishment model of pay-per-use and consumable products. Instead of purchasing a physical consumable component, the embodiments employ a pay-per-use model that limits the treatment time or usage of a handheld dermatological medical device, which must receive replenishment data in order to operate for continued use.

Figure 16:
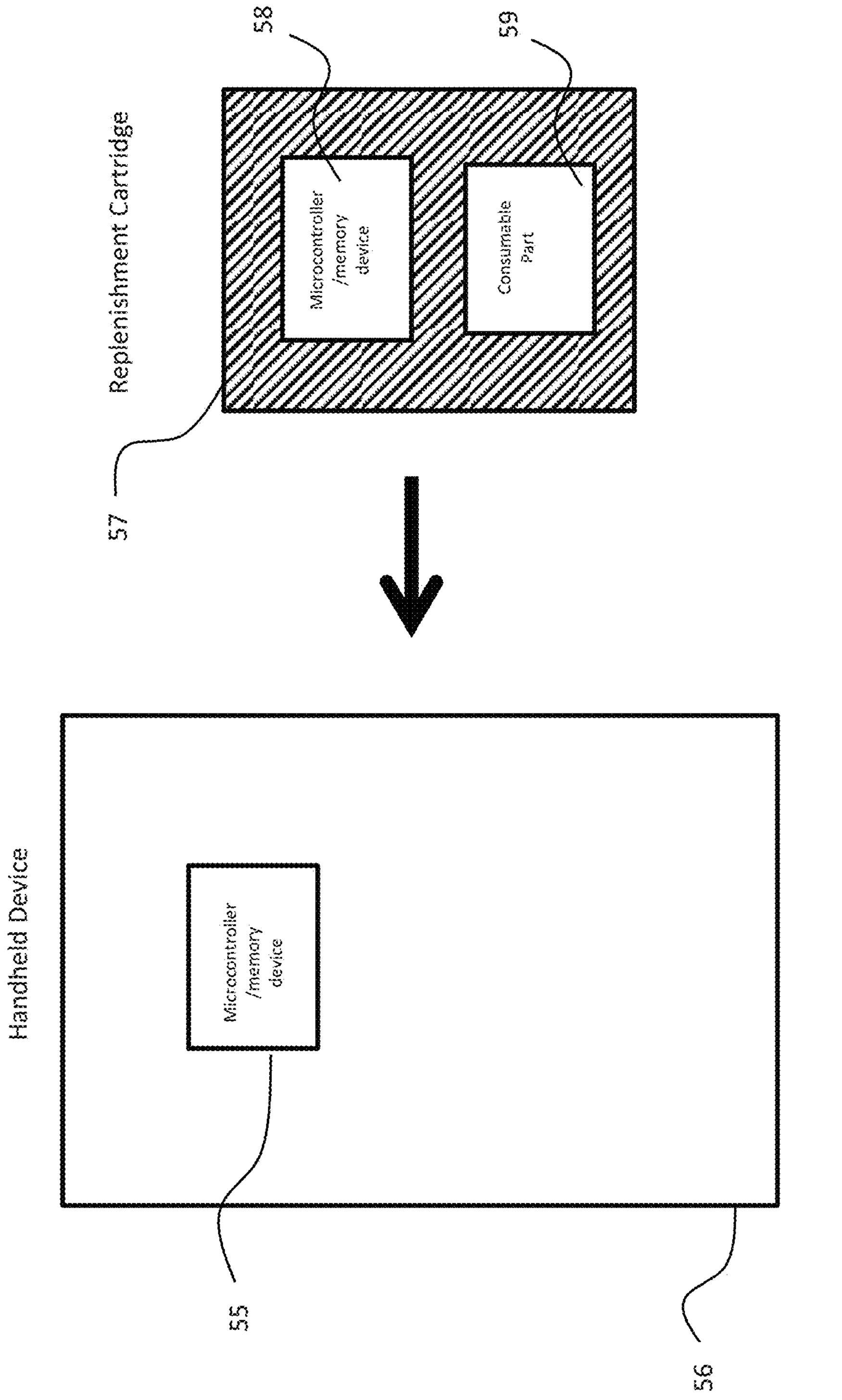
FIG. 16 is a block diagram of a handheld dermatological medical device constructed and arranged to communicate with a replenishment cartridge, in accordance with an embodiment.

FIG. 16 is a block diagram of a handheld dermatological medical device 56 constructed and arranged to communicate with a replenishment cartridge 57, in accordance with an embodiment. The handheld dermatological medical device 56 in accordance with some embodiments can be constructed and arranged to operate according to a method for replenishment, for example, described herein, which can permit a user to purchase a device such as the handheld dermatological medical device 56 at a low initial retail price, while being permitted to continually use the device 56 through low replenishment costs that fit within the target consumer's buying habits, which can be similar to those as purchasing consumable beauty products such as topicals, creams, moisturizers, and so on. The device 56 can be similar to a handheld dermatological medical device according to other embodiments herein, except that the device 56 includes a microcontroller 55 that communicates with a disposable replenishment cartridge 57. The replenishment cartridge 57 may be inserted into the device 56 or attached externally. In both cases, an electrical connector is used to provide an electrical connection between the device 56 and the replenishment cartridge 57.

The replenishment cartridge 57 comprises a microcontroller 58 and/or a consumable part 59. The consumable part 59 is comprised of electronic components that have a limited life, and can be replaced without disposing of the entire replenishment cartridge 57. Limited life components of the consumable part 59 can include but not be limited to batteries, power electronics, optical components and laser or light sources. Power electronic switchers such as metal-oxide-semiconductor field-effect transistors (MOSFETs) and bipolar transistors have reduced lifetimes when exposed to excessive operating parameters. Light sources such as lamps and laser diodes also have a finite life. The microcontroller 58 can monitor the operation of the consumable part 59 and communicate a consumable part 59 operation or failure to the device 56, for example, the microcontroller 55. In an embodiment the microcontroller 58 may determine the maximum life time of the consumable part 59. As an example, the consumable part 59 may include a fuse that is connected to the control electronics (not shown) of the device and is electrically in series with the optical energy source (not shown) of the device 56, thus completing the electrical circuit from the control electronics 9 to the optical energy source 8. Once the device 56 has exceeded a set maximum number of treatments, the microcontroller 58 can disable the replenishment cartridge 57 by blowing the fuse, thereby breaking the electrical connection between the optical energy source 8 and control electronics 9.

Figure 17B:
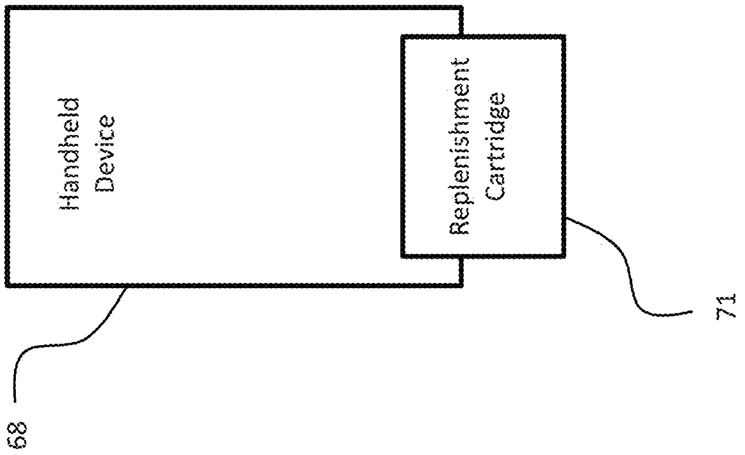
FIGS. 17A and 17B are block diagrams of different replenishment cartridge connection options, in accordance with some embodiments.
Figure 17A:
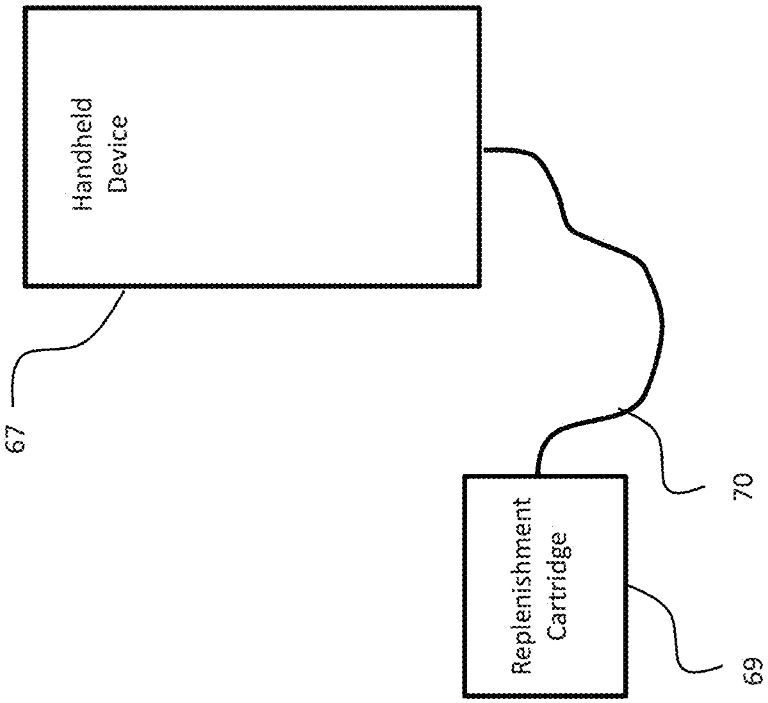

FIGS. 17A and 17B are block diagrams of different replenishment cartridge connection options, in accordance with some embodiments.

In a preferred embodiment, pay per use hardware replenishment can be achieved through replacement cartridges in communication with a handheld dermatological medical device. As shown in FIG. 17B, a replenishment cartridge 71 can be directly attached to a handheld dermatological medical device 68. For example, the handheld device 68 can include an inlet port or the like that removably couples to the replenishment cartridge 71 so that the device 68 within its housing can receive electronic data, power, and so on from the cartridge 71. In another embodiment, as shown in FIG.

Figure 18:
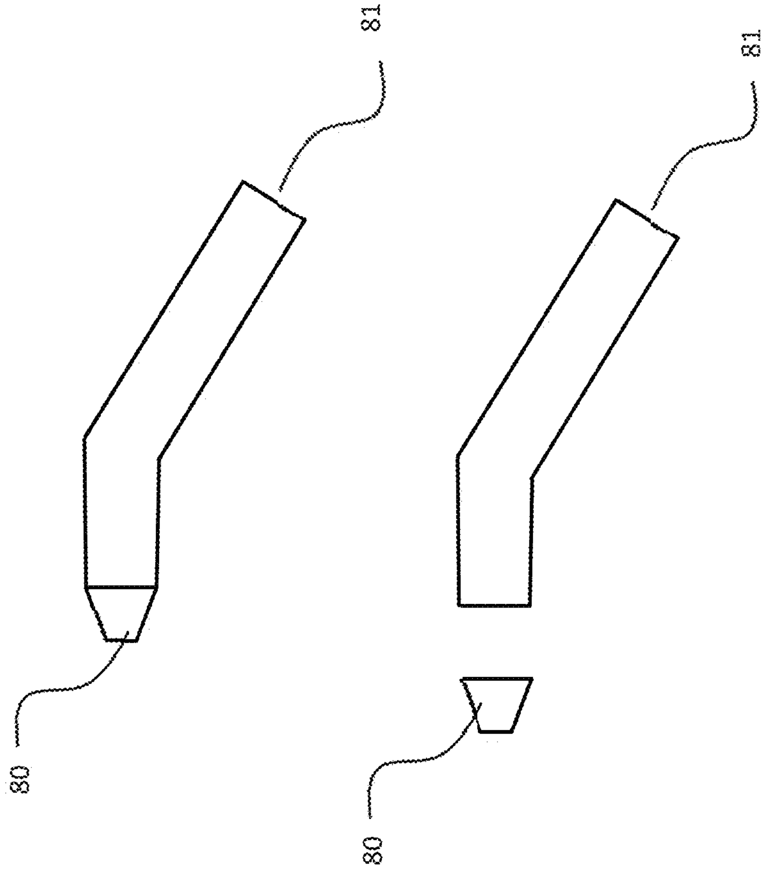
FIG. 18 is a view of a replenishment cartridge integrated into a treatment tip, in accordance with an embodiment.

17A, a replenishment cartridge 69 communicates with a handheld dermatological medical device 67 via a cable 70, or other communication medium known to those of ordinary skill in the art. Alternatively, a replenishment cartridge can be integrated into a functional component such as a disposable treatment tip 80 as shown in FIG. 18. In an embodiment, the disposable treatment tip 80 is removed from a non-disposable handheld member 81 and replaced with a new one when the replenishment cartridge expires, or more particular, a predetermined number of uses identified in the data in the replenishment cartridge in the treatment tip 80 expires. The device can therefore provide an amount of cleanliness or sanitary benefit when the handheld member 81 is used on multiple people, since a different treatment tip 80 can be provided for each person being treated.

Figure 19:
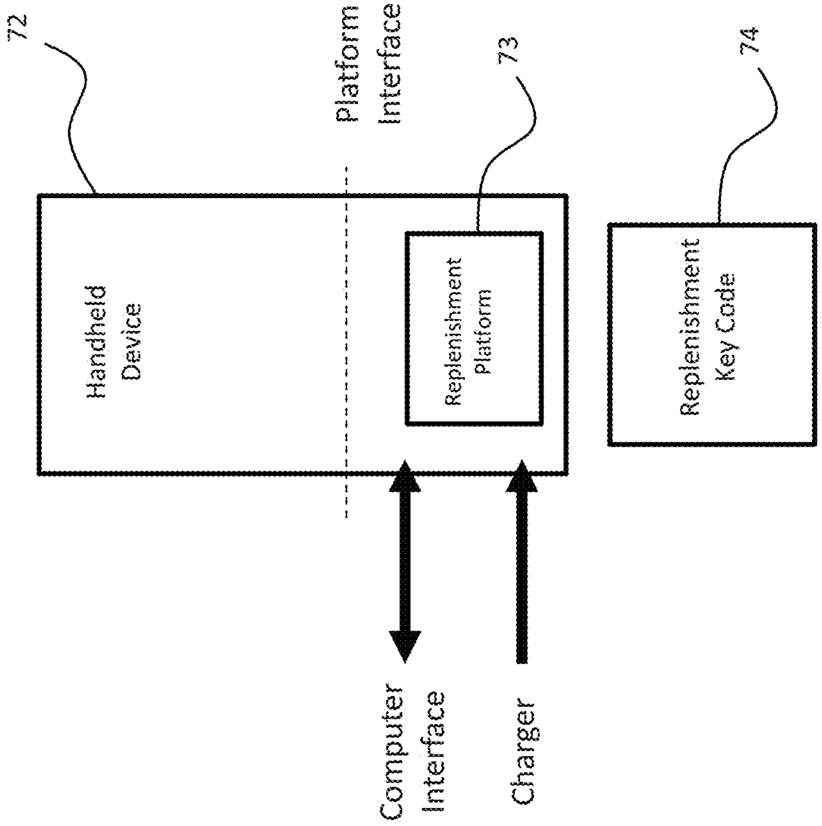
FIG. 19 is a block diagram of a handheld dermatological medical device including a key code replenishment platform, in accordance with an embodiment.

FIG. 19 is a block diagram of a handheld dermatological medical device 72 including a key code replenishment platform 73, in accordance with an embodiment. The handheld dermatological medical device 72 can be similar to one or more other handheld dermatological medical devices described herein, so details of the handheld dermatological medical device 72 are not repeated due to brevity.

The key code replenishment platform 73 of the device 72 includes a camera or RFID transceiver or the like for reading a replenishment keycode 74 such as an RFID, a barcode reader, a WiFi transmitter/receiver, a micro USB port, and/or other electronic device that can receive data related to the replenishment keycode 74. The replenishment platform 73 includes a processor that receives and processes the replenishment keycode 74 and outputs a signal to the control electronics of the device 72 for activating the device 72 for use. The replenishment keycode 74 can include data that establishes a number of uses, a timeframe during which unlimited use can occur, or other parameters that establish limited or unlimited use of the device 72.

Figure 20:
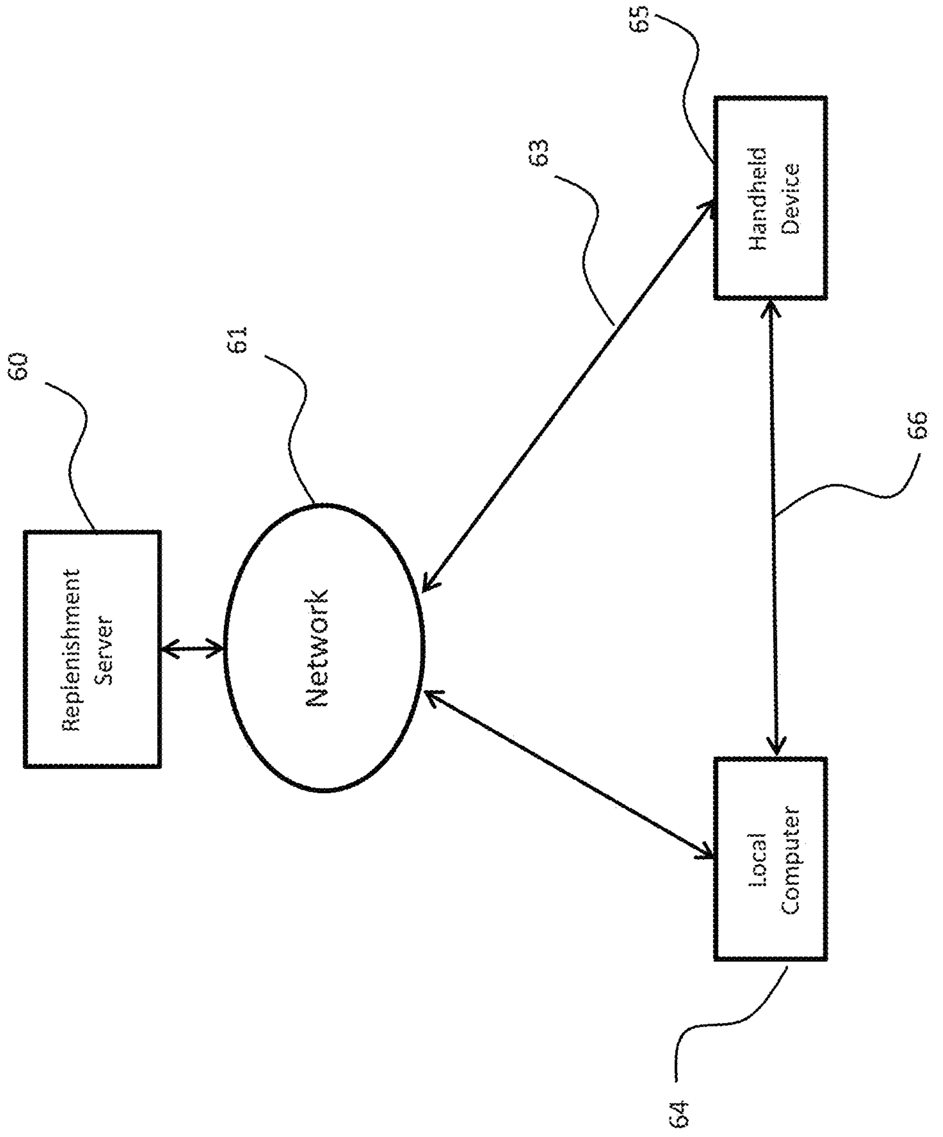
FIG. 20 illustrates a block diagram of a replenishment system communications environment, in accordance with an embodiment.

FIG. 20 illustrates a block diagram of a replenishment system communications environment, in accordance with an embodiment.

A pay-per-use electronic replenishment can be achieved through direct electronic communication between a replenishment server 60 and a handheld dermatological medical device 65. The handheld dermatological medical device 65 can be similar to one or more other handheld dermatological medical devices described herein, so details of the handheld dermatological medical device 65 are not repeated due to brevity.

The replenishment server 60 includes data related to the programming and activation/deactivation of the handheld dermatological medical device 65 with respect to use. For example, the replenishment server 60 can output data that is received by the device 65 that establishes unlimited use of the device 65 for 30 days. In another example, the replenishment server 60 can output data that is received by the device 65 that establishes a preconfigured number of treatments each for a predetermined amount of time, for example, 10 hourly treatments.

Communication between the remote replenishment server 60 and the handheld dermatological medical device 65 can be established through a network 61, such as a local area network, a wide area network, a wireless network, the internet, or a combination thereof. For example, a local computer 64 can be coupled to a router or other device via a connection 63 that establishes a communication with the network 61.

During operation, a key code replenishment can be delivered from the replenishment server 60 to a customer's computer 64 by means of an email or other communication. The consumer may enter the key code into the local computer 64. The local computer 64 can communicate via proprietary software program with the handheld dermatological medical device 65 via a USB cable 66 or other well-known electrical connector.

In an embodiment, the handheld dermatological medical device 65 communicates with a docking station, for example described herein, to receive power, replenishment data, for example, described herein, and/or other electronic data.

Figure 21:
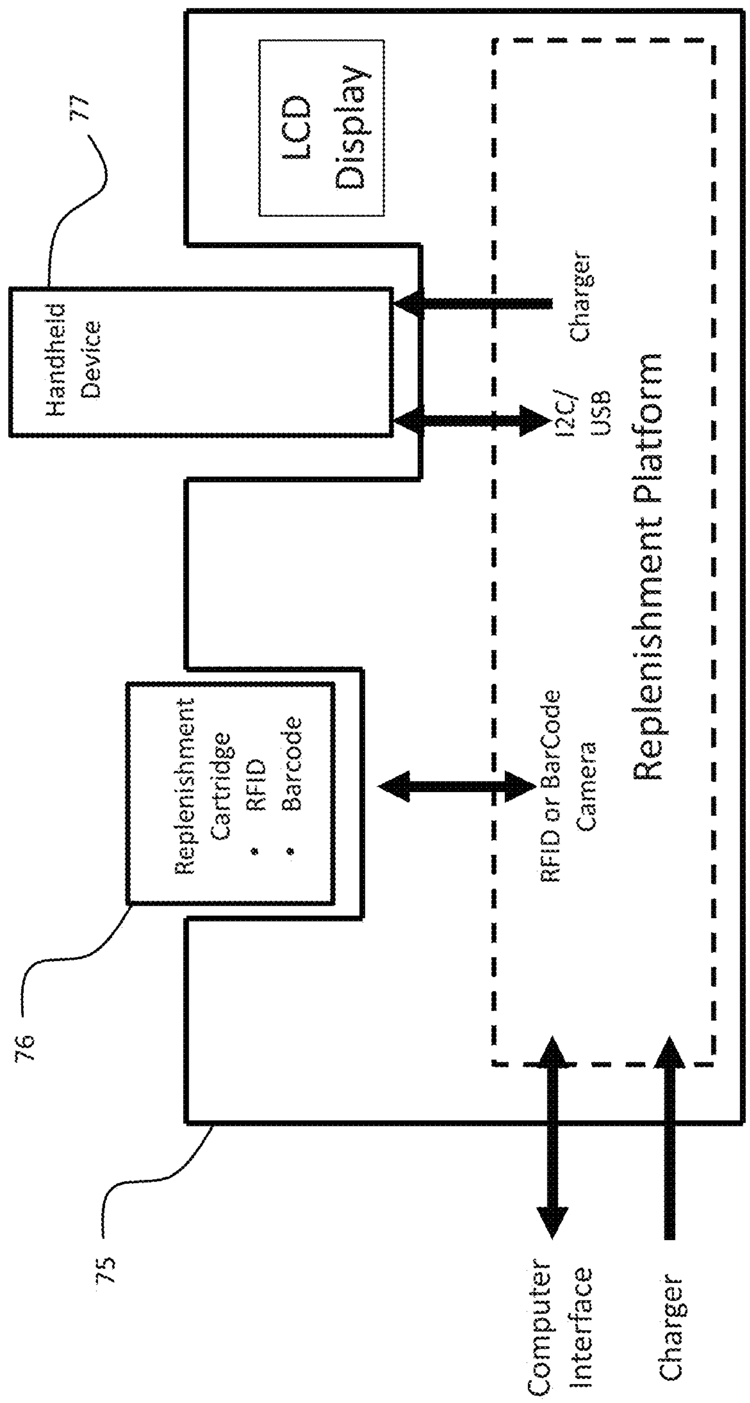
FIG. 21 illustrates a block diagram of a handheld dermatological medical device positioned in a docking station having a replenishment platform, in accordance with an embodiment.

FIG. 21 illustrates a block diagram of a handheld dermatological medical device 77 positioned in a docking station 75 having a replenishment platform, in accordance with an embodiment. The docking station 75 can be constructed and arranged to receive a replenishment cartridge 76 as well as the handheld dermatological medical device 77.

The handheld dermatological medical device 77 can be similar to one or more other handheld dermatological medical devices described herein. Therefore, details of the handheld dermatological medical device 77 are not repeated due to brevity.

In some embodiment, a replenishment cartridge 76 is inserted into docking station 75, instead of the device 77 as distinguished from other embodiments, for example, described herein.

The docking station 75 can include a computer interface, for example, a USB port, a charger, and/or other connector for communicating with external devices. The computer interface can provide for electronic replenishment, software updates, and/or other electronic exchange of data, power, etc.

The replenishment platform can include a camera or RFID transceiver or the like for reading a replenishment keycode 74 such as an RFID, a barcode reader, a WiFi transmitter/receiver, a micro USB port, and/or other electronic device that can receive data related to the replenishment cartridge 76. For example, when the cartridge 76 is removably coupled to the docking station 75, the replenishment platform can receive and process replenishment data, and output a signal to the control electronics of the handheld device 77 for activating the device 77 for use.

The docking station 75 can include a display such as a liquid-crystal display (LCD) that presents a visual status of the handheld device 77. For example, the LCD display can display a number of uses available before replenishment is required.

Figure 22:
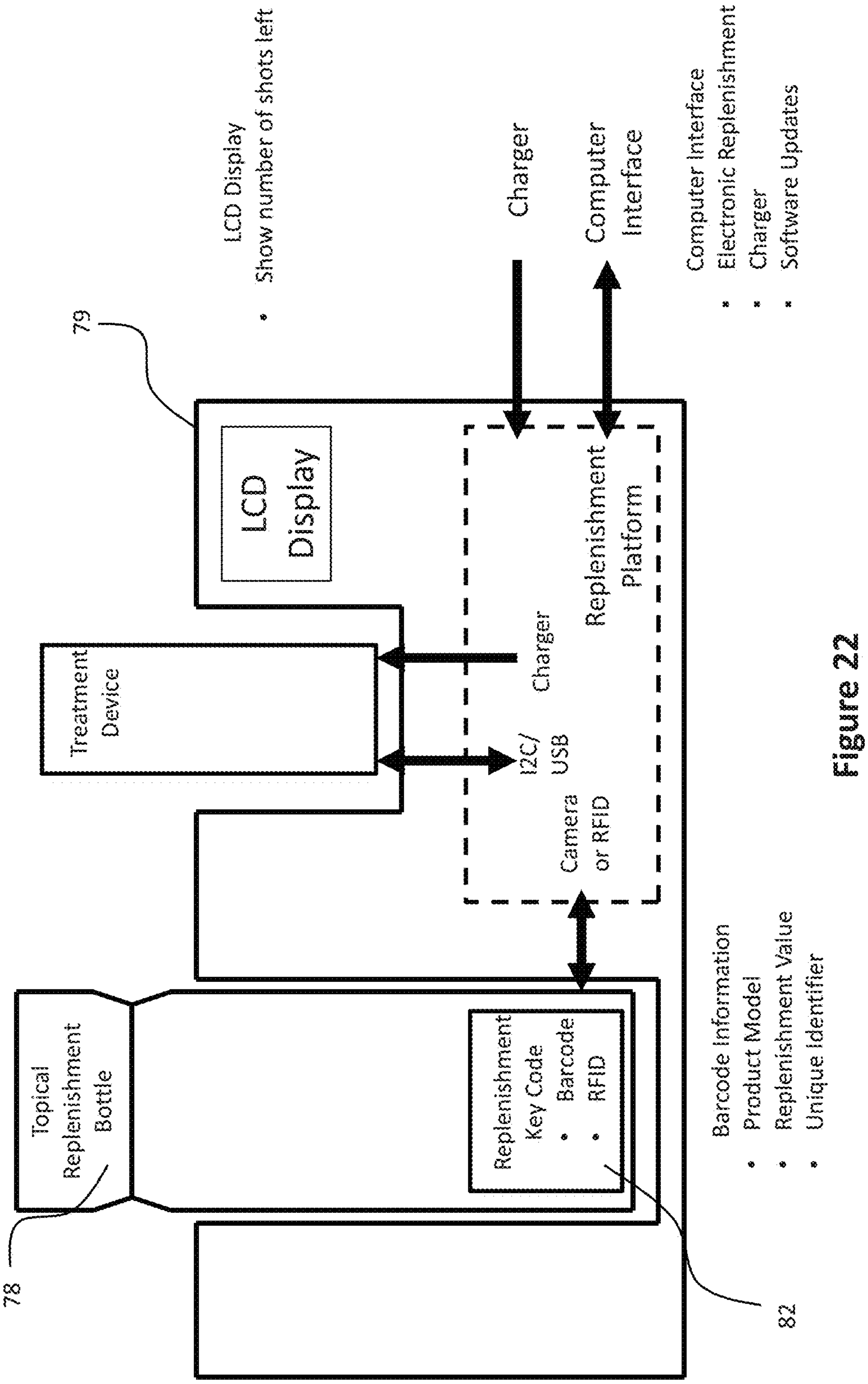
FIG. 22 illustrates a block diagram of a handheld dermatological medical device positioned in a docking station having a replenishment platform, in accordance with another embodiment.

FIG. 22 illustrates a block diagram of a handheld dermatological medical device 77 positioned in a docking station 79 having a replenishment platform, in accordance with another embodiment.

In an embodiment, the docking station 79 is constructed to receive a consumable such as a topical product 78 that includes a replenishment keycode 82 such as a barcode or RFID. The topical product 78 may be used adjunctively with the dermatological device during the treatment. This topical product 78 may be proprietary. The docking station 79 can read the keycode, barcode or RFID to authenticate the topical product 78. Barcode information can include a product model, replenishment value, and/or unique identifier. In cases where a counterfeit product may emerge, the use of the handheld dermatological medical device 77 is prevented. Additionally, the topical product 78 is consumed during its use. The handheld dermatological medical device 77 will stop functioning after a predetermined number of uses, an amount of time of use, or other operation parameters based upon the topical product's 78 keycode. Full operation of the handheld dermatological medical device 77 will only occur after the replenishment of topical product 78 through the purchase and installation of a new topical product 78 bottle.

Continued use of the handheld dermatological medical device 77 can be limited by the availability and access to replenishment distribution channels. Uninterrupted usage can also depend on the consumer's diligence in ensuring replenishment occurs prior to laser device running out of usage time or consumables. In a preferred embodiment, this business model offers a subscription to automatically provide replenishment in advance to prevent interrupted usage.

Figure 23:
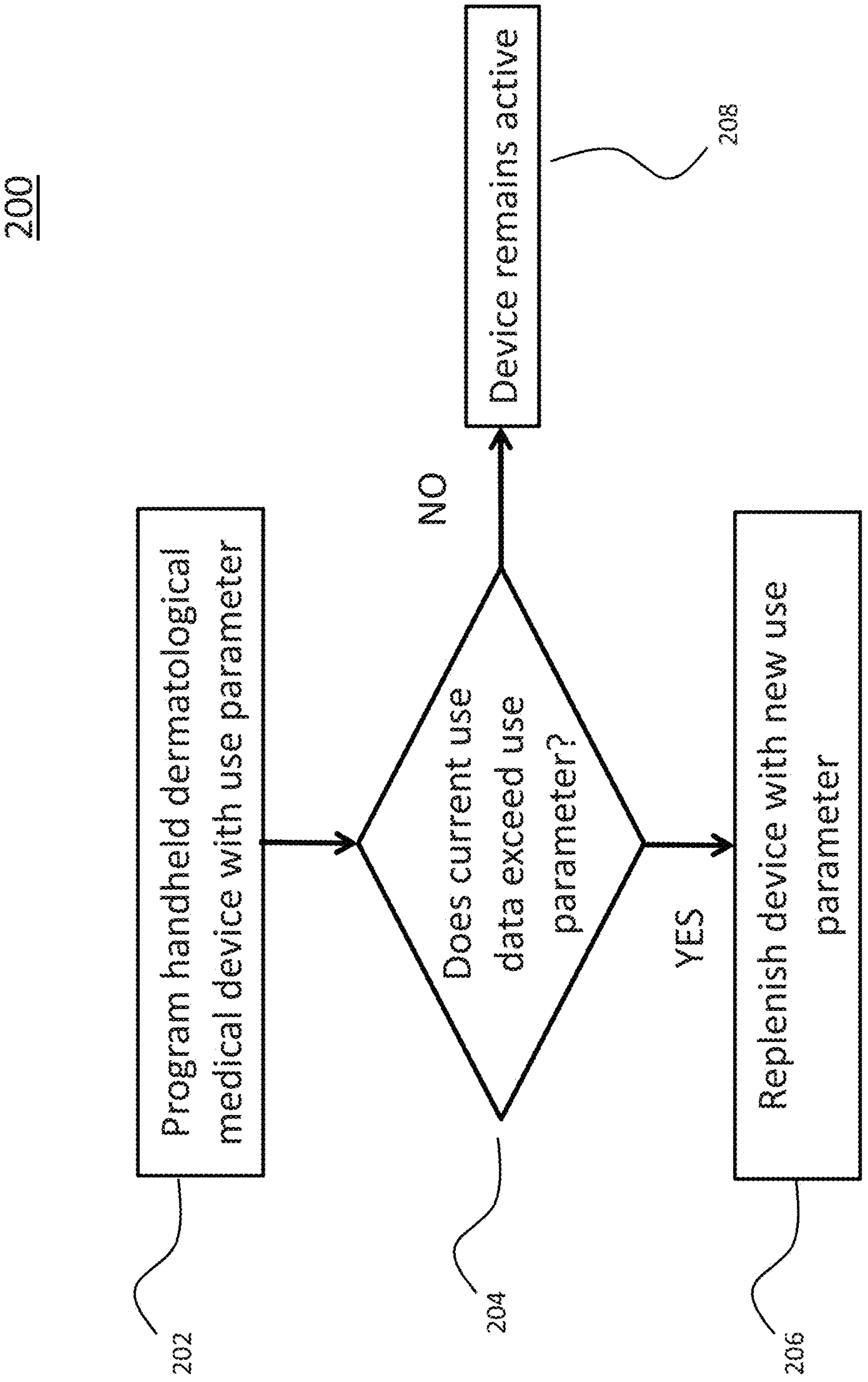
FIG. 23 is a flow diagram illustrating a method for replenishing a medical device for continued use, in accordance with an embodiment.

FIG. 23 is a flow diagram illustrating a method 200 for replenishing a medical device for continued use, in accordance with an embodiment. In describing FIG. 23, reference can be made to elements of other figures herein.

At block 202, a handheld dermatological medical device is programmed to include a use parameter. The use parameter can include a "refill" feature, for example, a number of permitted uses, an amount of time of use, or other finite replenishment value.

At decision diamond 204, a determination is made whether a current use value exceeds the programmable use parameter. If it is determined that the current use value exceeds the use parameter, then the method 200 proceeds to block 206, where the device can be programmed with a new use parameter, for example, replenished for a predetermined amount of continued use.

If it is determined that the current use value does not exceed the user parameter, then this indicates that there are sufficient treatment shots, i.e., individual uses, or available time for continued use, and the method 200 can proceed to block 208, where the device remains active until a determination is made that the device must be replenished for continued use.

Figure 24:
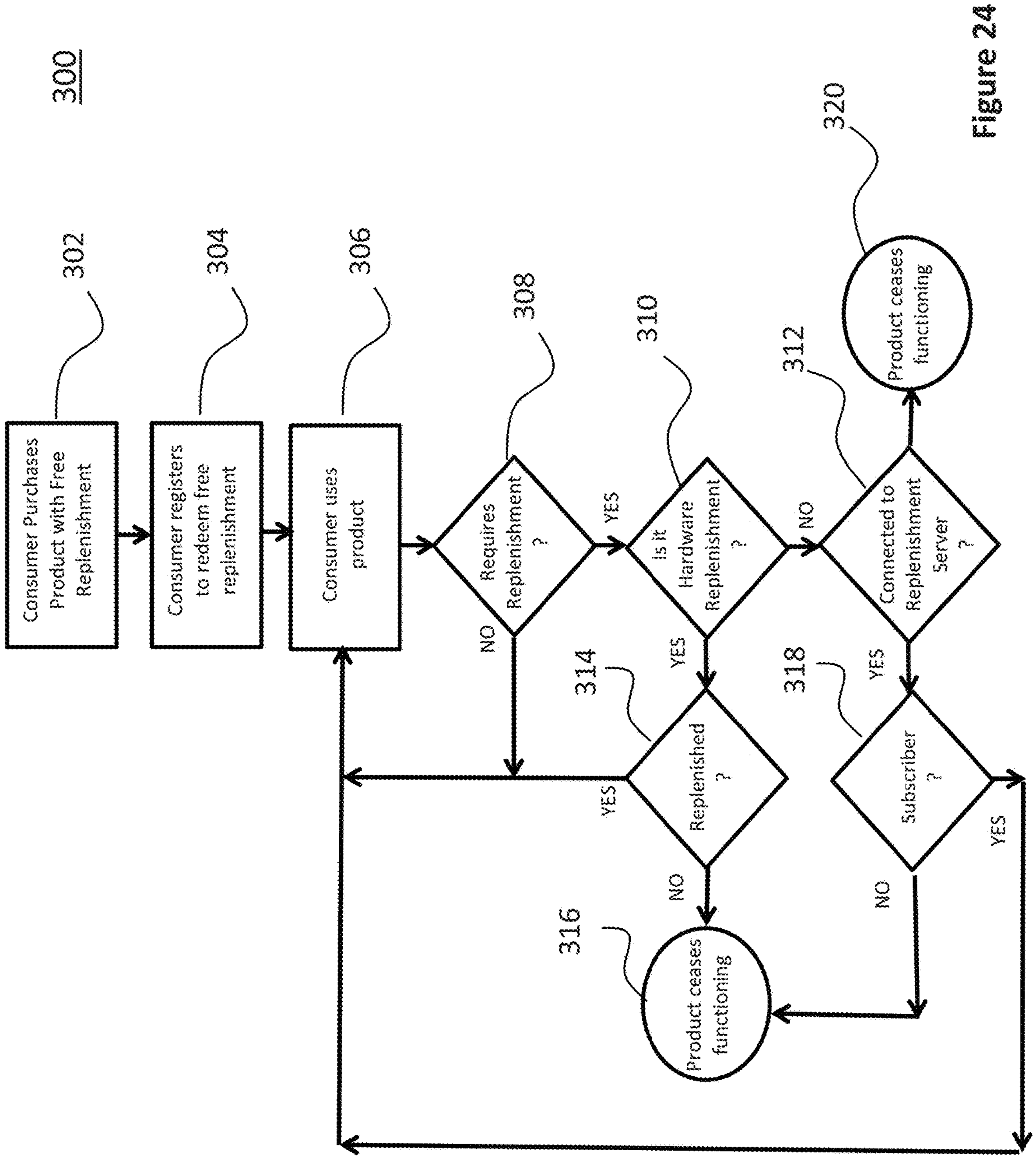
FIG. 24 is a flow diagram illustrating a method for replenishing a medical device for continued use, in accordance with an embodiment.

FIG. 24 is a workflow and functional flow diagram illustrating a method 300 for replenishing a medical device for continued use, in accordance with an embodiment. The medical device can include a handheld dermatological medical device, for example, described herein. Some or all of the method 300 can be performed at a handheld dermatological medical device, a replenishment server or platform, and/or other electronic device having at least a processor and storage device, for example, a memory.

At block 302, a consumer purchases a medical device having a finite usage life. The medical device preferably includes an electronic component that includes at least a processor and/or memory for storing data. The finite usage life of the medical device can include a predetermined number of treatment shots or an amount of time of use of the device. The device can be constructed and arranged to be prevented to operate when the final usage life is 0, and to operate when the usage life is greater than 0. In an embodiment, the product is initially configured with at least one free replenishment.

At block 304, in order to redeem the replenishment provided at block 302, the medical device is registered with the replenishment server. During registration, is the medical device can be provided with a subscription for automatic replenishment, for example, as shown in FIG. 24.

At block 306, the medical device can be operational for use. In an embodiment, the medical device is activated when the medical device is programmed with replenishment data, described herein. The medical device is inactivated when the medical device does not have replenishment data.

At decision diamond 308, a determination is made whether the medical device requires replenishment data. If yes, then the method 300 proceeds to decision diamond 310, where a determination is made whether the form of replenishment is hardware replenishment, for example, described herein, or at decision diamond 312, where a determination is made whether the medical device is in communication with a replenishment server, for example, described at FIG. 20. Returning to decision diamond 308, if a determination is made that the medical device does not require replenishment data, then the method 300 proceeds to block 306.

Returning to decision diamond 310, if a determination is made that the form of replenishment is hardware replenishment, then the method 300 proceeds to decision diamond 314, where a determination is made whether the medical device receives replenishment data, for example, including a predetermined number of uses, a period of time of use, and so on. If yes, then the method 300 proceeds to block 306. If no, then the method proceeds to block 316 where the medical device is inactivated, and ceases to function.

Returning to decision diamond 312, if a determination is made that the medical device is in communication with a replenishment server, then the method 300 proceeds to decision diamond 318, wherein a determination is made whether a subscriber is active. If no, then the method 300 proceeds to block 316, where the medical device is inactivated, and ceases to function. If yes, then the method 300 proceeds to block 306. If at decision diamond 312 a determination is made that the medical device is not in communication with a replenishment server, then the method proceeds to block 320, where the medical device is inactivated, and ceases to function.

Figure 25:
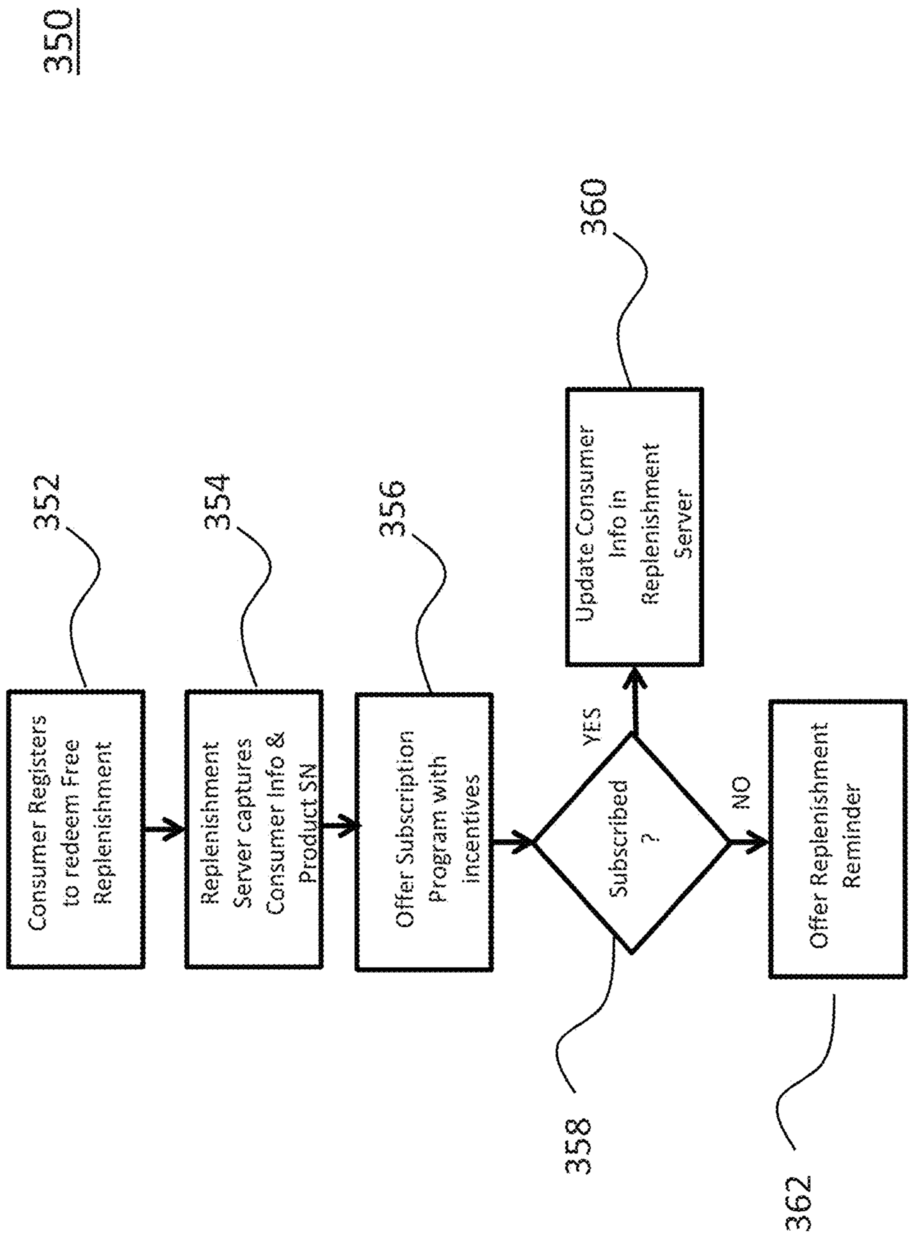
FIG. 25 is a flow diagram illustrating a method for replenishing a medical device for continued use, in accordance with an embodiment.

FIG. 25 is a flow diagram illustrating a method 350 for replenishing a medical device for continued use, in accordance with an embodiment. The medical device can include a handheld dermatological medical device, for example, described herein. Some or all of the method 300 can be performed at a handheld dermatological medical device, a replenishment server or platform, and/or other electronic device having at least a processor and storage device, for example, a memory.

At block 352, a consumer registers to redeem a free replenishment. In particular, the handheld dermatological medical device establishes an electronic communication with a replenishment server, device, or platform, for example, described herein.

At block 354, the replenishment server receives data such as consumer information, product serial number, and/or other relevant information, and stores it at a memory location.

At block 356, a subscription for automatic replenishment is provided. Information regarding the subscription can be electronically generated at the replenishment server or at a computer server or other electronic device separate from and in communication with the replenishment server. The subscription information can be displayed at an LCD display or the like for viewing by the user.

At decision diamond 358, a determination is made whether to accept the offer for a subscription. If the user decides to purchase or otherwise accepts to receive a subscription, then the method 350 proceeds to block 360, where an acceptance signal is generated, for example, from the handheld dermatological medical device and/or a remote computer processor, and output to the replenishment server. The acceptance signal includes consumer information, for example, described herein, and is stored at the replenishment server. Otherwise, the method 350 proceeds to block 362, where the replenishment server generates an electronic signal that includes data related to a reminder to replenish the handheld dermatological medical device for continued use.

While the present inventive concepts have been particularly shown and described above with reference to exemplary embodiments thereof, it will be understood by those of ordinary skill in the art, that various changes in form and detail can be made without departing from the spirit and scope of the present inventive concepts.

What is claimed is:

1. A method for non-injuring heat shock stimulation of human or animal tissue comprising:

positioning a distal end of a handheld dermatological medical device at a region proximal a target therapeutic region of tissue;

outputting optical energy from an optical laser of the handheld dermatological medical device at the target therapeutic region of tissue; and controlling the output of the optical energy at the target therapeutic region of tissue to increase a temperature of the target therapeutic region of tissue for a period of time between 20 ms and 10 seconds to a temperature range and induces an expression of heat shock proteins (HSPs) to increase the temperature of the target therapeutic region of tissue between 2-8 degrees C at the target therapeutic region of tissue, by outputting the optical energy at an average power density from 0.1 $W/cm^2$ by control electronics of the optical laser, wherein controlling the output of the optical energy comprises delivering the optical energy at a first power level during an initial heating phase sufficient to raise the temperature of the target therapeutic region of tissue to the temperature range that is less than an injuring temperature, and after the target therapeutic region of tissue reaches the temperature range, delivering the optical energy at a lower average power level during a temperature maintenance phase to maintain the temperature of the target therapeutic region of tissue within the temperature range, wherein the first power level corresponds to peak power density configured to increase tissue temperature, and the lower average power level corresponds to a maintenance power density configured to maintain tissue temperature within the temperature range, and wherein the initial heating phase and the temperature maintenance phase occur during the period of time between 20 ms and 10 seconds.

2. The method of claim 1, wherein an application of a handheld treatment member is selected from the group consisting of: wrinkle reduction; acne reduction; skin tightening; tissue heating; treatment of fibrous tissue; treatment of vascular tissue; and combinations thereof.

3. The method of claim 1, wherein the distal end of a handheld dermatological medical device includes an aperture, and wherein the handheld dermatological medical device includes at least one contact sensor that only allows the handheld dermatological medical device to operate when the aperture is in contact with the target therapeutic region of tissue.

4. The method of claim 1, where a wavelength is between 1850 nm-1900 nm.

5. The method of claim 1, where a wavelength is between 1900-2450 nm.

6. The method of claim 1, where a wavelength is between 1400-1900 nm.

7. The method of claim 1, wherein the steps of outputting the optical energy and controlling the output of the optical energy at the target therapeutic region of tissue are performed a plurality of treatment times, including a first treatment time and a second treatment time, each of the plurality of treatment times.

8. The method of claim 7, wherein the plurality of treatment times includes daily treatment times.

9. The method of claim 7, wherein a peak of the expression of HSPs occur 1.5 hours to 48 hours after the first treatment time, and the second treatment time is performed after the peak of the expression of HSPs.

10. The method of claim 1, wherein an exposure of the optical energy output from the dermatological medical device at the target therapeutic region of tissue is between 2-10 seconds at one or more temperatures less than an injuring temperature.

11. The method of claim 1, wherein the target therapeutic region of tissue includes intact undamaged skin.

12. The method of claim 1, wherein the target therapeutic region of tissue includes wrinkles, and wherein controlling the output of the optical energy at the target therapeutic region of tissue to induce the expression of heat shock proteins (HSPs) at the target therapeutic region of tissue including the wrinkles.

13. The method of claim 1, wherein maintaining the temperature of the target therapeutic region of tissue within the temperature range is achieved by reducing delivered optical power from the first power level to the lower average power level rather than by continued exposure at the first power level.

14. The method of claim 1, wherein the temperature maintenance phase produces a substantially steady tissue temperature plateau within the temperature range for a portion of the single treatment pulse.

15. A method for non-injuring heat shock stimulation of human or animal tissue comprising:

positioning a distal end of a handheld dermatological medical device at a region proximal a target therapeutic region of tissue;

outputting optical energy from an optical laser of the handheld dermatological medical device at the target therapeutic region of tissue; and controlling the output of the optical energy at the target therapeutic region of tissue to increase a temperature of the target therapeutic region of tissue for a period of time between 20 ms and 10 seconds to a temperature range and induces an expression of heat shock proteins (HSPs) to increase the temperature of the target therapeutic region of tissue between 2-8 degrees C at the target therapeutic region of tissue, and further outputting the optical energy at an average power density between 0.1 $W/cm^2$ and 0.37 $W/cm^2$ within the period of time between 20 ms and 10 seconds by control electronics of the optical laser to maintain the temperature of the target therapeutic region of tissue within the temperature range that is less than an injuring temperature.

16. A method for non-injuring heat shock stimulation of human or animal tissue comprising:

positioning a distal end of a handheld dermatological medical device at a region proximal a target therapeutic region of tissue;

outputting optical energy between 1400 nm and 1530 nm from an optical laser of the handheld dermatological medical device at the target therapeutic region of tissue; and controlling the output of the optical energy at the target therapeutic region of tissue to increase a temperature of the target therapeutic region of tissue for a period of time between 20 ms and 10 seconds to a temperature range that is less than an injuring temperature and induces an expression of heat shock proteins (HSPs) to increase the temperature of the target therapeutic region of tissue between 2-8 degrees C at the target therapeutic region of tissue, by outputting the optical energy at an average power density from 0.1 W/cm$^2$ by control electronics of the optical laser, wherein controlling the output of the optical energy comprises delivering the optical energy at a first power level during an initial heating phase sufficient to raise the temperature of the target therapeutic region of tissue to the temperature range that is less than the injuring temperature, and after the target therapeutic region of tissue reaches the temperature range, delivering the optical energy at a lower average power level during a temperature maintenance phase to maintain the temperature of the target therapeutic region of tissue within the temperature range, wherein the first power level corresponds to peak power density configured to increase tissue temperature, and the lower average power level corresponds to a maintenance power density configured to maintain tissue temperature within the temperature range, and wherein the initial heating phase and the temperature maintenance phase occur during the period of time between 20 ms and 10 seconds.

17. The method of claim 16, wherein an application of a handheld treatment member is selected from the group consisting of: wrinkle reduction; acne reduction; skin tightening; tissue heating; treatment of fibrous tissue; treatment of vascular tissue; and combinations thereof.

18. The method of claim 16, wherein the distal end of the handheld dermatological medical device includes an aperture, and wherein the handheld dermatological medical device includes at least one contact sensor that only allows the handheld dermatological medical device to operate when the aperture is in contact with the target therapeutic region of tissue.

19. The method of claim 16, wherein the steps of outputting the optical energy and controlling the output of the optical energy at the target therapeutic region of tissue are performed a plurality of treatment times, including a first treatment time and a second treatment time, each of the plurality of treatment times.

20. The method of claim 16, wherein a plurality of treatment times includes daily treatment times.

21. The method of claim 16, wherein an exposure of the optical energy output from the dermatological medical device at the target therapeutic region of tissue is between 2-10 seconds at one or more temperatures less than the injuring temperature.

22. The method of claim 16, wherein the target therapeutic region of tissue includes intact undamaged skin.

23. The method of claim 16, wherein the target therapeutic region of tissue includes wrinkles, and wherein controlling the output of the optical energy at the target therapeutic region of tissue to induce the expression of heat shock proteins (HSPs) at the target therapeutic region of tissue including the wrinkles.

24. The method of claim 16, wherein the target therapeutic region of tissue naturally cool downs by passive means including the tissue itself to decrease the temperature of the target therapeutic region of tissue after inducing the expression of HSPs.

25. The method of claim 16, wherein maintaining the temperature of the target therapeutic region of tissue within the temperature range is achieved by reducing delivered optical power from the first power level to the lower average power level rather than by continued exposure at the first power level.

26. The method of claim 16, wherein the temperature maintenance phase produces a substantially steady tissue temperature plateau within the temperature range for a portion of the single treatment pulse.

27. A method for non-injuring heat shock stimulation of human or animal tissue comprising:

positioning a distal end of a handheld dermatological medical device at a region proximal a target therapeutic region of tissue;

outputting optical energy between 1400 nm and 1530 nm from an optical laser of the handheld dermatological medical device at the target therapeutic region of tissue; and controlling the output of the optical energy at the target therapeutic region of tissue to increase a temperature of the target therapeutic region of tissue for a period of time between 20 ms and 10 seconds to a temperature range that is less than an injuring temperature and induces an expression of heat shock proteins (HSPs) to increase the temperature of the target therapeutic region of tissue between 2-8 degrees C at the target therapeutic region of tissue, and further outputting the optical energy at an average power density between 0.1 W/cm$^2$ and 0.37 W/cm$^2$ within the period of time between 20 ms and 10 seconds by control electronics of the optical laser to maintain the temperature of the target therapeutic region of tissue within the temperature range that is less than the injuring temperature.

* * * * *